(12) United States Patent
Olson

(10) Patent No.: US 12,343,337 B2
(45) Date of Patent: Jul. 1, 2025

(54) COMPOUNDS FOR INCREASING NEURAL PLASTICITY

(71) Applicant: THE REGENTS OF THE UNIVERSITY OF CALIFORNIA, Oakland, CA (US)

(72) Inventor: David E. Olson, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/337,698

(22) PCT Filed: Sep. 29, 2017

(86) PCT No.: PCT/US2017/054277
§ 371 (c)(1),
(2) Date: Mar. 28, 2019

(87) PCT Pub. No.: WO2018/064465
PCT Pub. Date: Apr. 5, 2018

(65) Prior Publication Data
US 2020/0030309 A1  Jan. 30, 2020

Related U.S. Application Data

(60) Provisional application No. 62/401,641, filed on Sep. 29, 2016.

(51) Int. Cl.
*A61K 31/4045* (2006.01)
*A61K 31/404* (2006.01)
(Continued)

(52) U.S. Cl.
CPC ........ *A61K 31/454* (2013.01); *A61K 31/4045* (2013.01); *A61K 31/4196* (2013.01); *A61K 31/422* (2013.01)

(58) Field of Classification Search
CPC .......................... A61K 31/4045; A61K 31/404
See application file for complete search history.

(56) References Cited

U.S. PATENT DOCUMENTS 3,525,750 A   8/1970   Renner
3,553,232 A   1/1971   Hester
(Continued)

FOREIGN PATENT DOCUMENTS

AU     614343 B2      8/1991
CA     2715282 A1 *   8/2009   .............. A61P 15/10
(Continued)

OTHER PUBLICATIONS

Meintzschel, Frank et al., "Modification of Practice-dependent Plasticity in Human Motor Cortex by Jeuromodulators", Cerebral Cortex, vol. 16, Oct. 12, 2015, pp. 106-1115. (Year: 2015).*
(Continued)

*Primary Examiner* — Craig D Ricci
*Assistant Examiner* — Janet L Coppins
(74) *Attorney, Agent, or Firm* — Mintz, Levin, Cohn, Ferris, Glovsky and Popeo, P.C

(57) ABSTRACT

The present invention provides a method of using non-hallucinogenic analogs of psychedelic compounds for increasing neural plasticity of the neuronal cell, and a method of using thereof for treating a brain disorder.

4 Claims, 11 Drawing Sheets

(51) Int. Cl.
    *A61K 31/4196*     (2006.01)
    *A61K 31/422*     (2006.01)
    *A61K 31/454*     (2006.01)

(56) References Cited

U.S. PATENT DOCUMENTS

| | | | |
|---|---|---|---|
| 3,637,744 | A | 1/1972 | Yardley et al. |
| 3,652,588 | A | 3/1972 | Hester |
| 4,478,750 | A | 10/1984 | Gadient |
| 4,581,354 | A | 4/1986 | Bell |
| 4,841,056 | A | 6/1989 | Hunter |
| 5,068,234 | A | 11/1991 | D'Ambra et al. |
| 5,219,859 | A | 6/1993 | Festal et al. |
| 5,494,928 | A | 2/1996 | Bos |
| 5,627,077 | A | 5/1997 | Dyllick-brenzinger et al. |
| 5,843,682 | A | 12/1998 | Sigler et al. |
| 5,852,046 | A | 12/1998 | Lang et al. |
| 6,017,945 | A | 1/2000 | Rawson et al. |
| 6,380,238 | B1 | 4/2002 | Adams et al. |
| 6,380,242 | B1 | 4/2002 | Arora et al. |
| 6,407,092 | B1 | 6/2002 | Hester et al. |
| 6,468,999 | B1 | 10/2002 | Jacobsen et al. |
| 6,548,493 | B1 | 4/2003 | Robichaud et al. |
| 6,552,017 | B1 | 4/2003 | Robichaud et al. |
| 6,635,639 | B2 | 10/2003 | Arora et al. |
| 6,828,314 | B2 | 12/2004 | Frank et al. |
| 6,903,090 | B2 | 6/2005 | Frank et al. |
| 8,338,447 | B2 | 12/2012 | Hung et al. |
| 8,367,655 | B2 | 2/2013 | Rajagopalan |
| 9,481,676 | B2 | 11/2016 | Hung et al. |
| 10,583,123 | B2 | 3/2020 | Yang et al. |
| 11,697,651 | B2 | 7/2023 | Muratore et al. |
| 2002/0022616 | A1 | 2/2002 | Fu |
| 2002/0169322 | A1 | 11/2002 | Arora et al. |
| 2002/0173503 | A1 | 11/2002 | Robichaud et al. |
| 2003/0199491 | A1 | 10/2003 | Hennequin |
| 2003/0212055 | A1 | 11/2003 | Hennequin |
| 2003/0220321 | A1 | 11/2003 | Frank et al. |
| 2003/0225058 | A1 | 12/2003 | Frank et al. |
| 2003/0232828 | A1 | 12/2003 | Bernotas et al. |
| 2003/0236278 | A1 | 12/2003 | Bernotas et al. |
| 2004/0023947 | A1 | 2/2004 | Martin et al. |
| 2004/0092502 | A1 | 5/2004 | Fevig et al. |
| 2004/0242884 | A1 | 12/2004 | Larsen et al. |
| 2005/0070558 | A1 | 3/2005 | Vidal Juan et al. |
| 2005/0250767 | A1 | 11/2005 | Weiner et al. |
| 2006/0105030 | A1 | 5/2006 | Windt-Hanke et al. |
| 2006/0148808 | A1 | 7/2006 | Robichaud et al. |
| 2006/0199829 | A1 | 9/2006 | Anandan et al. |
| 2006/0247228 | A1 | 11/2006 | Umeda et al. |
| 2007/0197603 | A1 | 8/2007 | Consonni et al. |
| 2007/0213359 | A1 | 9/2007 | Burstein et al. |
| 2007/0254875 | A1 | 11/2007 | Zhi et al. |
| 2009/0318446 | A1 | 12/2009 | Fischer et al. |
| 2010/0152163 | A1 | 6/2010 | Hung et al. |
| 2010/0317863 | A1 | 12/2010 | Kuzmich et al. |
| 2011/0003793 | A1 | 1/2011 | Guzzo et al. |
| 2011/0003836 | A1 | 1/2011 | Mcknight et al. |
| 2011/0003840 | A1 | 1/2011 | Rajagopalan |
| 2011/0229555 | A1 | 9/2011 | Helson et al. |
| 2011/0245222 | A1 | 10/2011 | Payan et al. |
| 2012/0245161 | A1 | 9/2012 | Choi-sledeski et al. |
| 2012/0296569 | A1 | 11/2012 | Shahaf et al. |
| 2013/0040977 | A1 | 2/2013 | Mcknight et al. |
| 2013/0178618 | A1 | 7/2013 | Boulanger |
| 2013/0190293 | A1 | 7/2013 | Chakravarty et al. |
| 2013/0195866 | A1 | 8/2013 | Bacskai et al. |
| 2013/0217675 | A1 | 8/2013 | Chakravarty et al. |
| 2013/0225558 | A1 | 8/2013 | Chakravarty et al. |
| 2014/0155384 | A1 | 6/2014 | Protter et al. |
| 2014/0206711 | A1 | 7/2014 | Chakravarty et al. |
| 2014/0228353 | A1 | 8/2014 | Protter et al. |
| 2014/0275531 | A1 | 9/2014 | Bollu et al. |
| 2014/0275548 | A1 | 9/2014 | Basinger et al. |
| 2014/0296209 | A1 | 10/2014 | Protter et al. |
| 2014/0303144 | A1 | 10/2014 | Protter et al. |
| 2014/0343018 | A1 | 11/2014 | Mcknight et al. |
| 2015/0057301 | A1 | 2/2015 | Mcknight et al. |
| 2015/0141345 | A1 | 5/2015 | Gozes et al. |
| 2015/0266884 | A1 | 9/2015 | Protter et al. |
| 2016/0002237 | A1 | 1/2016 | Rajagopalan |
| 2018/0263964 | A1 | 9/2018 | Bamdad et al. |
| 2020/0087305 | A1 | 3/2020 | Tomesch et al. |
| 2020/0375967 | A1 | 12/2020 | Stamets |
| 2022/0251040 | A1 | 8/2022 | Olson et al. |
| 2022/0304980 | A1 | 9/2022 | Arnold et al. |
| 2023/0117791 | A1 | 4/2023 | Olson et al. |
| 2023/0150963 | A1 | 5/2023 | Baggott |
| 2023/0202965 | A1 | 6/2023 | Short et al. |
| 2023/0295106 | A1 | 9/2023 | Olson et al. |
| 2024/0208973 | A1 | 6/2024 | Olson et al. |

FOREIGN PATENT DOCUMENTS

| | | |
|---|---|---|
| CN | 102977091 A | 3/2013 |
| CN | 102977092 A | 3/2013 |
| EP | 0473550 A1 | 3/1992 |
| GB | 20550110 A | 11/2017 |
| JP | 2017031088 A | 2/2017 |
| NL | 6515701 A | 6/1966 |
| WO | 9423720 A1 | 10/1994 |
| WO | 9524200 A1 | 9/1995 |
| WO | 9840102 A1 | 9/1998 |
| WO | 2000038677 | 7/2000 |
| WO | 0064899 A1 | 11/2000 |
| WO | 2001070223 | 9/2001 |
| WO | 2004064738 A2 | 8/2004 |
| WO | 2004005389 A1 | 11/2005 |
| WO | 2007118314 | 10/2007 |
| WO | 2008117935 A1 | 10/2008 |
| WO | 2008157845 A1 | 12/2008 |
| WO | 2009035473 A2 | 3/2009 |
| WO | 2009036996 | 3/2009 |
| WO | 2009103022 A1 | 8/2009 |
| WO | 2011103433 A1 | 8/2011 |
| WO | 2012112966 A1 | 8/2012 |
| WO | 2012154261 | 11/2012 |
| WO | 2013007698 A2 | 10/2013 |
| WO | 2017216279 A1 | 12/2017 |
| WO | 2018045178 A1 | 3/2018 |
| WO | 2018209341 A1 | 11/2018 |
| WO | 2019099402 A1 | 5/2019 |
| WO | 2020169851 A1 | 8/2020 |
| WO | 2020176597 A1 | 9/2020 |
| WO | 2020176599 A1 | 9/2020 |
| WO | 2020181050 A1 | 9/2020 |
| WO | 2020181194 A1 | 9/2020 |
| WO | 2020186027 A1 | 9/2020 |
| WO | 2021076572 | 4/2021 |
| WO | 2021178691 A1 | 9/2021 |
| WO | 2022020352 A1 | 1/2022 |
| WO | 2022051670 A1 | 3/2022 |
| WO | 2022067165 A1 | 3/2022 |
| WO | 2022081631 A1 | 4/2022 |
| WO | 2022120181 A1 | 6/2022 |
| WO | 2022120475 A1 | 6/2022 |
| WO | 2022170268 A1 | 8/2022 |
| WO | 2022221415 A2 | 10/2022 |
| WO | 2022246554 A1 | 12/2022 |
| WO | 2023283364 A2 | 1/2023 |
| WO | 2023018480 A1 | 2/2023 |
| WO | 2023018864 A1 | 2/2023 |
| WO | 2023023298 A1 | 2/2023 |
| WO | 2023059546 A1 | 4/2023 |
| WO | 2023073423 A1 | 5/2023 |
| WO | 2023077127 A2 | 5/2023 |
| WO | 2023081306 A1 | 5/2023 |
| WO | 2023081753 A1 | 5/2023 |
| WO | 2023092195 A1 | 6/2023 |
| WO | 2023108164 A2 | 6/2023 |
| WO | 2023108165 A2 | 6/2023 |
| WO | 2023108174 A1 | 6/2023 |
| WO | 2023114472 A1 | 6/2023 |
| WO | 2023115006 A1 | 6/2023 |

(56) References Cited

FOREIGN PATENT DOCUMENTS

| WO | 2023115060 | A1 | 6/2023 |
|---|---|---|---|
| WO | 2023115165 | A1 | 6/2023 |
| WO | 2023115166 | A1 | 6/2023 |
| WO | 2023122135 | A1 | 6/2023 |
| WO | 2024059495 | | 3/2024 |

OTHER PUBLICATIONS

Anderson, Chemistry & Biology 2003, vol. 10, pp. 787-797. (Year: 2003).*
Printout of National Institute of Mental Health website: https://www.nimh.nih.gov/health/topics/depression/index.shtml, 2018, pp. 1-13. (Year: 2018).*
Thiel, Nature Biotechnology 2004, vol. 22(5), pp. 513-519. (Year: 2004).*
Tittarelli et al, Current Neuropharmacology 2015, vol. 13, pp. 26-46. (Year: 2015).*
Meyer et al, Am. J. Psychiatry 2001,, vol. 158, pp. 78-85. (Year: 2001).*
Fitzgerald et al, J. Neurochem 1999. 72, 21 27-21 34. (Year: 1999).*
Glennon et al, Drug & Alcohol Dependence 2000, vol. 60, pp. 121-132. (Year: 2000).*
Masuda and Sugiyama, Tohoku J Exp Med 2000, vol. 1911, pp. 47-54. (Year: 2000).*
Sanches et al, J Clin Psychopharmacol, Feb. 2016;36: 77-81 (Year: 2016).*
Marek et al., The Journal of Pharmacology and Experimental Therapeutics 1989, 250(1), pp. 60-71. (Year: 1989).*
Ray, Thomas. PLoS One (2010), 5(2), pp. 1-17. (Year: 2010).*
Goadsby et al., "1533 Comparative efficacy of Eletriptan and Sumatriptan in reducing recurrence in high-risk migraine patients", Abstract.
Lieberman et al., "Use of Lisuride in Advanced Parkinson's Disease Potent Dopamine and Serotonin Agonist", new York State Journal of Medicine, Medical Society of the State of New York, NY, US, vol. 81, No. 12, Nov. 1, 1981, pp. 1751-1755.
Luquin et al., "Parenteral administration of lisuride in Parkinson's disease", Advances in Neurology, Raven Press, New York, US, Jan. 1, 1987, vol. 45, pp. 561-568.
European Search Report for EP Application 17857489.3 mailed Apr. 8, 2020, 6 pages.
Hougaku et al., "Therapeutic Effect of Lisuride maleate on Poststroke Depression", Jpn J Geriat, Jan. 1994, vol. 31, pp. 52-59; Abstract, p. 59.
Konopaske et al., "Prefrontal Cortical Dendritic Spine Pathology in Schizophrenia and Bipolar disorder", JAMA Psychiatry, Dec. 2014, 71(12):1323-1331.
Moyer et al., "Dendritic spine alterations in schizophrenia", Neuroscience Letters 601, 2015, pp. 46-53.
Nakamura et al., "Effects in animal models of depression of lisuride along and upon co-administration with antidepressants", Folia pharmacol. japon., 1989, 94(1):81-89; Abstract, p. 89.
Penzes et al., "Dendritic spine pathology in neuropsychiatric disorders", Nature Neuroscience Review, Mar. 2011, vol. 14, No. 3, pp. 285-293.
Antonaci, Fabio et al., "Recent advances in migraine therapy", SpringerPlus, May 17, 2016, p. 637.
Borovac, Josip Andelo, "Side effects of a dopamine agonist therapy for Parkinson's disease: a mini-review of clinical pharmacology", Yale Journal of Biology and Medicine, vol. 89, Mar. 24, 2016, pp. 37-47.
Chiba, Shuichi et al., "Cabergoline, a dopamine receptor agonist, has an antidepressant-like property and enhances prain-derived neurotrophic factor signaling", Psychopharmacology vol. 211, May 23, 2010, pp. 291-301.
Harris, M.D., Ph.D., Yael T., "Cabergoline Associated with First Episode Mania", Psychosomatics, vol. 53, May 31, 2012, pp. 595-600.
Meintzschel, Frank et al., "Modification of Practice-dependent Plasticity in Human Motor Cortex by Neuromodulators", Cerebral Cortex, vol. 16, Oct. 12, 2015, pp. 1106-1115.
Odaka, Haruki et al., "Cabergoline, Dopamine D2 Receptor Agonist, Prevents Neuronal Cell Death under Oxidative Stress via Reducing Excitotoxicity", PLoS One, vol. 9, Jun. 10, 2016, pp. 1-12.
Pfizer Canada, Inc., "Product Monograph", Pfizer Cananda Inc., Jul. 23, 2013, pp. 1-2.
Sharma, Gitanjali, "Intranasal Cabergoline: Pharmacokinetic and Pharmacodynamic Studies", AAPS PHarSciTech, vol. 10, No. 4, Nov. 6, 2009, pp. 1321-1330.
International Search Report in PCT/US2017/054277 mailed Dec. 14, 2017.
Written Opinion of the International Searching Authority in PCT/US2017/054277 mailed Dec. 14, 2017.
Izumi et al., "Open pergolide treatment of tricyclic and heterocyclic antidepressant-resistant depression," Journal of Affective Disorders, 61, pp. 127-132 (2000).
Pubchem (Aug. 8, 2005) "Carbazole, 9-(1-methyl-2-piperidyl) methyl-", PubChem CID 43403, 10 pages.
International Search Report and Written Opinion received for International Application No. PCT/US2020/019856, mailed on Jun. 26, 2020, 11 pages.
International Search Report and Written Opinion received for International Application No. PCT/US2020/019858, mailed on Jul. 15, 2020, 12 pages.
Cameron et al.(Jan. 21, 2021) "A Non-hallucinogenic Psychedelic Analogue With Therapuetic Potential", Nature, 589:474-479(24 pages).
Cameron et al. (Jul. 2019) "Chronic, Intermittent Microdoses of the Psychedelic N,N-Dimethyltryptamine (DMT) Produce Positive Effects on Mood and Anxiety in Rodents", ACS Chemical Neuroscience, 10(7):3261-3270.
Cameron et al. (Oct. 2018) "Dark Classics in Chemical Neuroscience: N,N-Dimethyltryptamine (DMT)", ACS Chemical Neuroscience, 9(10):2344-2357.
Cameron et al. (Jul. 2018) "Effects of N,N-Dimethyltryptamine on Rat Behaviors Relevant to Anxiety and Depression", ACS Chemical Neuroscience, 9(7):1582-1590(22 pages).
Cameron et al. (Apr.-Jun. 2020) "Psychedelic Microdosing: Prevalence and Subjective Effects", Jounal of Psychoactive Drugs, 52(2):113-122.
Dunlap et al. (Jan. 2020) "Identification of Psychoplastogenic N,N-Dimethylaminoisotryptamine (isoDMT) Analogues through Structure—Activity Relationship Studies", Journal of Medicinal Chemistry, 63(3):1142-1155(36 pages).
Glennon et al. (1983) "DOM-stimulus Generalization to LSD and other Hallucinogenic Indolealkylamines", European Journal of Pharmacology, 86:453-459.
Golda et al. (Jun. 1987) "Animal Model of Depression: Drug Induced Changes Independent of Changes in Exploratory Activity", Activitas nervosa superior, 29(2):114-115.
Golda et al. (Mar. 1986) "Animal Model of Depression: Imipramine, Bromocriptine and Lisuride Alleviate Motor Depression", Activitas Nervosa Superior, 28(1):26-27(4 pages).
Golda et al. (1986) "Reactivity to the Electric Shocks and Motor Depression as a Consequence of Inescapable Shocking: the Effect of Acute Lisuride Treatment", 27(4):377-392.
Halford (Dec. 2020) "Ibogaine Inspires Potential Neuropsychiatric Treatment", C&E News, 3 pages.
Ly et al. (Jun. 12, 2018) "Psychedelics Promote Structural and Functional Neural Plasticity", Cell Reports, 23(11):3170-3182.
PubChem (Oct. 20, 2014) "1,2,3,4-Tetrahydropyrrolo[2,3-b]Indole", PubChem CID 82415753, 8 pages.
Zetler et al. (1972) "Refractory Period and Strophanthin Actions, as Influenced by Four Indole Alkaloids and Two Synthetic Azepinoindoles", Pharmacology, 8:235-243.
PubChem (Jun. 16, 2016) "3,4-Trimethylen-inden", PubChem SID 314981250, 5 pages.
International Search Report and Written Opinion received for International Application No. PCT/US2020/055507, mailed on Mar. 1, 2021, 12 pages.

(56) References Cited

OTHER PUBLICATIONS

Glennon et al., "Synthesis and Evaluation of a Novel Series of N,N-Dimethylisotryptamines", J. Med. Chem. 1984, 27, 41-45.
Chang-Fong et al., "Evaluation of Isotryptamine Derivatives at 5-HT2 Serotonin Receptors", Bioorg. Med. Chem. Lett. 2002, 12, 155-158.
U.S. Appl. No. 17/345,471, filed Jun. 11, 2021, "N-Substituted Indoles And Other Heterocycles For Treating", 157 pages.
U.S. Appl. No. 17/345,745, filed Jun. 11, 2021, "Azepino-indoles And Other Heterocycles For Treating Brain Disorders", 119 pages.
Vargas, "Psychedelics and Other Psychoplastogens for Treating Mental Illness" Frontiers in Psychiatry 2021, p. 1-19.
Third Party Observations received for European Application No. 17857489.3, mailed on Feb. 15, 2022, 2 pages.
Hester et al. (Jan. 1, 1968) "Azepinoindoles. I. Hexahydroazepino[4,5-b] indoles", Journal of Medicinal Chemistry, 11:101-106.
Pumphrey et al. (Jun. 11, 2012) "RhII2-Catalyzed Synthesis of α-, β-, or δ-Carbolines from Aryl Azides", Angewandte Chemie International Edition, 51(24): 5920-5923 (10 pages).
Zetler et al. (Jan. 1968) "Die Wirkung von 11 Indol-Alkaloiden auf das Meerschweinchen-Herz in vivo und in vitro, verglichen mit 2 synthetischen Azepinoindolen, Chinidin und Quindonium", Naunyn-Schmiedebergs Archiv für Pharmakologie und experimentelle Pathologie, 260, 26-49.
Zetler et al. (1970) "Inhibition of Cardiac Effects of Noradrenaline by Eleven Indole Alkaloids, Two Azepinoindoles, Quinidine, Quindonium, and Propranolol", Pharmacology, 4:129-142.
International Search Report and Written Opinion for PCT/US2022/024626, mailed Jul. 1, 2022, 9 pages.
Abate et al. (2005) "Interaction of Chiral MS-245 Analogs at h5-HT6 Receptors", Bioorganic & Medicinal Chemistry Letters, 15(15):3510-3513.
Eiter et al. (1952) "Zur Konstitution des Folicanthius", Monatshefte Fur Chemie-Chemical Monthly, 83(6):1453-1476.
Lacivita et al. (2006) "Selective Agents For Serotonin (2C) (5-HT2C) Receptor", Current Topics in Medicinal Chemistry, 6(18):1927-1970.
Seki, Teruya (1967) "Studies on 2-benzimidazolethiol Derivatives. V. Structure-activity Relationship on Analgesic Action of 1-(dialkylamino-alkyl)-2-(p-ethoxyphenylthio)benzimidazole", Journal of the Pharmaceutical Society of Japan, 87(3):301-309.
Supplementary European Search Report received in Application No. 20763824.8 mailed on Nov. 3, 2022, 3 pages.
Zubenko et al. (Apr. 17, 2019) "Pyridine-Azepine Structural Modification of 3,4-Dihydro-nor-isoharmine", Russian Journal of Organic Chemistry, 55(1):74-82.
(Aug. 16, 2002) Chemical Abstracts Services, CAS Registry No. 405312-66-5, 2 pages.
(Dec. 26, 2004) Chemical Abstracts Services, CAS Registry No. 802581-10-8, 2 pages.
(Jan. 10, 2013) Chemical Abstracts Services, CAS Registry No. 1416330-38-5, 2 pages.
(Nov. 16, 1984) Chemical Abstracts Services, CAS Registry No. 7546-69-2, 2 pages.
(Nov. 16, 1984) Database Registry, Chemical Abstracts Services, CAS Registry No. 7546-76-1, 2 pages.
(Nov. 16, 1984) Database Registry, Chemical Abstracts Services, CAS Registry No. 7546-73-8, 2 pages.
(Nov. 16, 1984) Database Registry, Chemical Abstracts Services, CAS Registry No. 7546-75-0, 2 pages.
(Nov. 27, 2012) Chemical Abstracts Services, CAS Registry No. 1407483-64-0, 2 pages.
(Nov. 16, 1984) Database Registry, Chemical Abstracts Services, CAS Registry No. 7546-72-7, 2 pages.
International Search Report and Written Opinion for PCT/US2022/079217, mailed Feb. 1, 2023, 9 pages.
International Search Report and Written Opinion for PCT/US2022/081927, mailed Apr. 17, 2023, 11 pages.
(2016) Pubchem-SID-274223890, 5 pages.
Chen et al. (Apr. 2022) "Iboga-type Alkaloids with Indolizidino[8,7-b]Indole Scaffold and Bisindole Alkaloids from Tabernaemontana Bufalina Lour", Phytochemistry, 196:113089.
Church et al. (2013) "'Ecstasy' Enhances Noise-induced Hear", Hearing Research, 302:96-106.
Dong et al. (May 13, 2021) "Psychedelic-inspired Drug Discovery Using an Engineered Biosensor", Cell, 184(10):2779-2792.e18.
Huang et al. (2005) "Comparison of the Use of Aqueous and Nonaqueous Buffers in Association with Cyclodextrin for the Chiral Separation of 3,4-methylenedioxymethamphetamine and Related Compounds", Electrophoresis, 26(20):3904-3909.
Pieroni et al. (2015) "Rational Design and Synthesis of Thioridazine Analogues as Enhancers of the Antituberculosis Therapy", Journal of medicinal chemistry, 58(15):5842-5853 (43 pages).
Whitehouse et al. (2019) "Development of Inhibitors against *Mycobacterium abscessus* tRNA (m1G37) Methyltransferase (TrmD) Using Fragment-Based Approaches", Journal of medicinal chemistry, 62(15):7210-7232.
Blair et al., "Effect of ring fluorination on the pharmacology of hallucinogenic tryptamines", J. Med. Chem. 2000, 43(24), 4701-10.
Carman et al., "Negative effects of melatonin on depression", Am J. Psychiatry 1976, 133(10), 1181-6.
Colley, "This Is What It Feels Like to Treat Depression with Magic Mushrooms", Vice.com (https://www.vice.com/en/article/8gk5wz/microdosing-psilocybin-depression-184), Sep. 7, 2015.
Database Registry, Chemical Abstracts Services, CAS Registry No. 2072109-30-7 (Entered STN: Feb. 17, 2017).
Database Registry, Chemical Abstracts Services, CAS Registry No. 2072109-20-5 (Entered STN: Feb. 17, 2017).
Database Registry, Chemical Abstracts Services, CAS Registry No. 1785609-23-5 (Entered STN: Jun. 21, 2015).
Database Registry, Chemical Abstracts Services, CAS Registry No. 1784120-59-7 (Entered STN: Jun. 19, 2015).
Database Registry, Chemical Abstracts Services, CAS Registry No. 1782881-47-3 (Entered STN: Jun. 17, 2015).
Database Registry, Chemical Abstracts Services, CAS Registry No. 1781908-34-6 (Entered STN: Jun. 17, 2015).
Database Registry, Chemical Abstracts Services, CAS Registry No. 1781904-21-9 (Entered STN: Jun. 17, 2015).
Database Registry, Chemical Abstracts Services, CAS Registry No. 1781798-70-6 (Entered STN: Jun. 17, 2015).
Database Registry, Chemical Abstracts Services, CAS Registry No. 1781710-62-0 (Entered STN: Jun. 17, 2015).
Database Registry, Chemical Abstracts Services, CAS Registry No. 1779925-03-9 (Entered STN: Jun. 14, 2015).
Database Registry, Chemical Abstracts Services, CAS Registry No. 1540652-24-1 (Entered STN: Feb. 10, 2014).
Database Registry, Chemical Abstracts Services, CAS Registry No. 1540077-46-0 (Entered STN: Feb. 9, 2014).
Database Registry, Chemical Abstracts Services, CAS Registry No. 1533998-25-2 (Entered STN: Jan. 30, 2014).
Database Registry, Chemical Abstracts Services, CAS Registry No. 1533723-14-6 (Entered STN: Jan. 30, 2014).
Database Registry, Chemical Abstracts Services, CAS Registry No. 1525468-14-7 (Entered STN: Jan. 20, 2014).
Database Registry, Chemical Abstracts Services, CAS Registry No. 1524903-93-2 (Entered STN: Jan. 20, 2014).
Database Registry, Chemical Abstracts Services, CAS Registry No. 1523634-22-1 (Entered STN: Jan. 19, 2014).
Database Registry, Chemical Abstracts Services, CAS Registry No. 1521620-08-5 (Entered STN: Jan. 16, 2014).
Database Registry, Chemical Abstracts Services, CAS Registry No. 1519408-31-1 (Entered STN: Jan. 14, 2014).
Database Registry, Chemical Abstracts Services, CAS Registry No. 1516490-69-9 (Entered STN: Jan. 10, 2014).
Database Registry, Chemical Abstracts Services, CAS Registry No. 1515565-33-9 (Entered STN: Jan. 9, 2014).
Database Registry, Chemical Abstracts Services, CAS Registry No. 1515073-46-7 (Entered STN: Jan. 9, 2014).
Database Registry, Chemical Abstracts Services, CAS Registry No. 1514378-08-5 (Entered STN: Jan. 8, 2014).
Database Registry, Chemical Abstracts Services, CAS Registry No. 1513937-46-6 (Entered STN: Jan. 8, 2014).

(56) References Cited

OTHER PUBLICATIONS

Database Registry, Chemical Abstracts Services, CAS Registry No. 1513834-45-1 (Entered STN: Jan. 7, 2014).
Database Registry, Chemical Abstracts Services, CAS Registry No. 1509251-72-2 (Entered STN: Jan. 2, 2014).
Database Registry, Chemical Abstracts Services, CAS Registry No. 1505385-98-7 (Entered STN: Dec. 27, 2013).
Database Registry, Chemical Abstracts Services, CAS Registry No. 1503723-45-2 (Entered STN: Dec. 25, 2013).
Database Registry, Chemical Abstracts Services, CAS Registry No. 1502739-86-7 (Entered STN: Dec. 24, 2013).
Database Registry, Chemical Abstracts Services, CAS Registry No. 1501213-32-6 (Entered STN: Dec. 23, 2013).
Database Registry, Chemical Abstracts Services, CAS Registry No. 1499823-45-8 (Entered STN: Dec. 20, 2013).
Database Registry, Chemical Abstracts Services, CAS Registry No. 1347326-94-6 (Entered STN: Dec. 2, 2011).
Database Registry, Chemical Abstracts Services, CAS Registry No. 780030-99-1 (Entered STN: Nov. 14, 2004).
Database Registry, Chemical Abstracts Services, CAS Registry No. 778568-40-4 (Entered STN: Nov. 11, 2004).
Database Registry, Chemical Abstracts Services, CAS Registry No. 770702-18-6 (Entered STN: Oct. 28, 2004).
Database Registry, Chemical Abstracts Services, CAS Registry No. 757934-75-1 (Entered STN: Oct. 7, 2004).
Database Registry, Chemical Abstracts Services, CAS Registry No. 755746-20-4 (Entered STN: Oct. 1, 2004).
Database Registry, Chemical Abstracts Services, CAS Registry No. 736129-10-5 (Entered STN: Aug. 31, 2004).
Database Registry, Chemical Abstracts Services, CAS Registry No. 685503-57-5 (Entered STN: May 24, 2004).
Database Registry, Chemical Abstracts Services, CAS Registry No. 405311-77-5 (Entered STN: Apr. 16, 2002).
Database Registry, Chemical Abstracts Services, CAS Registry No. 405305-95-5 (Entered STN: Apr. 16, 2002).
Database Registry, Chemical Abstracts Services, CAS Registry No. 405305-92-2 (Entered STN: Apr. 16, 2002).
Database Registry, Chemical Abstracts Services, CAS Registry No. 15923-19-0 (Entered STN: Nov. 16, 1984).
Database Registry, Chemical Abstracts Services, CAS Registry No. 15918-91-9 (Entered STN: Nov. 16, 1984).
Database Registry, Chemical Abstracts Services, CAS Registry No. 15918-68-0 (Entered STN: Nov. 16, 1984).
Database Registry, Chemical Abstracts Services, CAS Registry No. 15918-67-9 (Entered STN: Nov. 16, 1984).
Third Party Observations, Europe Appl. No. 17857489.3, of Jan. 10, 2024, 7 pages.
Nichols, "Dark Classics in Chemical Neuroscience: Lysergic Acid Diethylamid (Lsd)", ACS Chem. Neurosci. 2018, 9, 2331-2343.
PubChem-SID-368776104, modify date May 25, 2018, p. 2, Fig. 2.
PubChem-SID-441175770, modify date Apr. 22, 2021, p. 2.
Turton et al., "A qualitative report on the subjective experience of intravenous psilocybin administered in an FMRI environment", Curr Drug Abuse Rev. 2014, 7(2), 117-27.
Unknown (2005). Chapter 11: Serotonin and Histamine. In Shao Fuyuan and Wang Yuhui (Eds.), Molecular Neuropharmacology (4th ed., pp. 261-263). Shanghai Science and Technology Press.
Unknown (2015). Chapter 5: Pathogenesis of Alzheimer's disease and progress in drug research. In Wang X. (Ed.), Practical Molecular Pharmacology (2nd ed., pp. 127). Peking Union Medical College Press. ISBN 978-7-5679-0411-8.
International Search Report and Written Opinion for PCT/US2023/073837, mailed Jan. 26, 2024, 9 pages.

\* cited by examiner

COMPOUNDS FOR INCREASING NEURAL PLASTICITY

CROSS-REFERENCES TO RELATED APPLICATIONS

This application is the U.S. National Stage Entry under § 371 of International Application No. PCT/US2017/054277, filed Sep. 29, 2017, which claims priority to U.S. Provisional Applications No. 62/401,641, filed Sep. 29, 2016, each of which is incorporated herein in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

Neuropsychiatric diseases, including mood and anxiety disorders, are some of the leading causes of disability worldwide and place an enormous economic burden on society. Approximately ⅓ of patients will not respond to current antidepressant drugs, and those who do will usually require at least 2-4 weeks of treatment before they experience any beneficial effects. Evidence from a combination of human imaging, postmortem studies, and animal models suggest that atrophy of neurons in the prefrontal cortex (PFC) plays a key role in the pathophysiology of depression and related disorders. These structural changes, such as the retraction of neurites and loss of dendritic spines, can potentially be counteracted by compounds capable of promoting structural and functional neural plasticity. Recently the nonclassical psychedelic ketamine has shown remarkable clinical potential as a fast-acting antidepressant and anxiolytic, exhibiting efficacy in treatment-resistant populations. Animal models suggest that its therapeutic effects stem from its ability to promote the growth of dendritic spines, increase the synthesis of synaptic proteins, and strengthen synaptic responses.

Clinical studies have demonstrated the potential for using classical psychedelics to treat a variety of neuropsychiatric disorders including depression, anxiety, addiction, and post-traumatic disorders. However, their therapeutic mechanism of action remains poorly understood, and concerns about safety have severely limited their clinical usefulness. Considering this, there is urgent need for the development of non-hallucinogenic analogs of psychedelics to treat a variety of brain disorders.

Described herein, inter alia, are solutions to these and other problems in the art.

BRIEF SUMMARY OF THE INVENTION

In one aspect, provided herein is a method of increasing neural plasticity. The method includes contacting a neuronal cell with a non-hallucinogenic analog of a psychedelic compound, in an amount sufficient to increase neural plasticity of the neuronal cell, wherein the non-hallucinogenic analog of a psychedelic compound produces a maximum number of dendritic crossings with an increase of greater than 1.0 fold by a Sholl Analysis.

In another aspect, provided herein is a method of treating a brain disorder. The method includes administering to a subject in need thereof a therapeutically effective amount of a non-hallucinogenic analog of a psychedelic compound, thereby treating the brain disorder, wherein the non-hallucinogenic analog of a psychedelic compound increases neural plasticity of the neuronal cell; provided that the subject is not already being treated with one or more of the following:

Ergometrine for postpartum hemorrhage and postabortion hemorrhage due to uterine atony;
Dihydroergotamine for migraines or cluster headaches;
Methylergometrine for routine management after delivery of the placenta, postpartum atony and hemorrhage, subinvolution, or migraines;
Methysergide for migraines or cluster headaches;
Ergotamine for migraines or cluster headaches;
Cabergoline for hyperprolactinemic disorders or Parkinson's disease;
Pergolide for Parkinson's disease;
Lisuride for Parkinson's disease;
Nicergoline for senile dementia or other disorders with vascular origins;
Bromocriptine for pituitary tumors, Parkinson's disease, hyperprolactinaemia, neuroleptic malignant syndrome, or type 2 diabetes; or
Sumatriptan, Zolmitriptan, Rizatriptan, Eletriptan, Naratriptan, Frovatriptan, or Almotriptan for migraines or cluster headaches.

DETAILED DESCRIPTION OF THE INVENTION

I. General

Figure 1A:
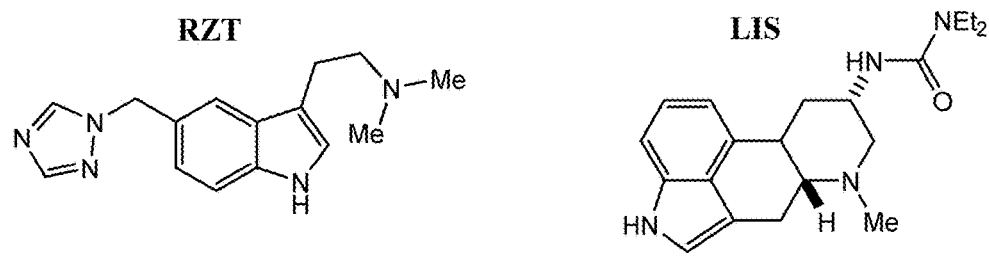
FIG. 1A shows chemical structures of Rizatriptan (RZT) and Lisuride (LIS).
Figure 1B:
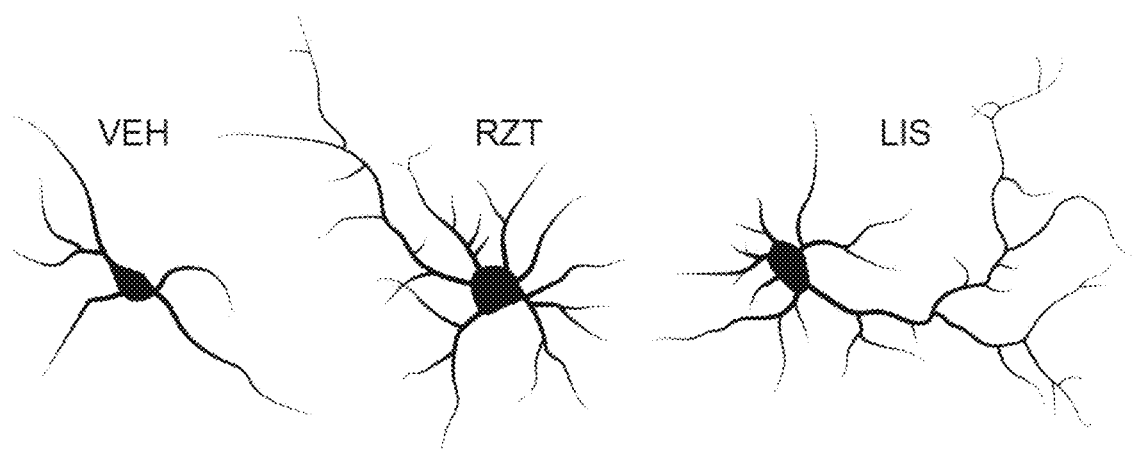
FIG. 1B shows representative tracings of cultured embryonic rat cortical neurons (DIV6) treated with compounds.
Figure 1C:
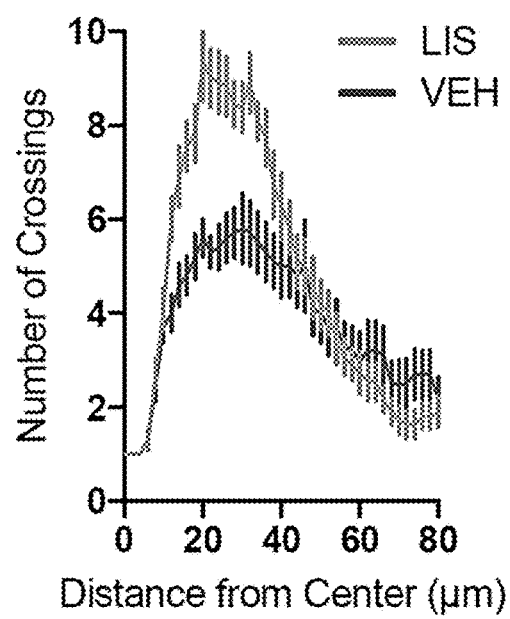
FIG. 1C shows Sholl plots by Sholl analysis (circle radii=2 μm increments) (n=9-11 neurons per treatment, DIV6).
Figure 1C:
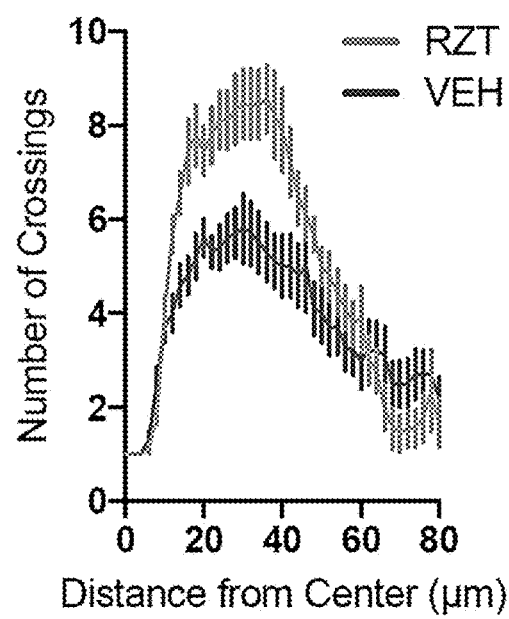
Figure 1D:
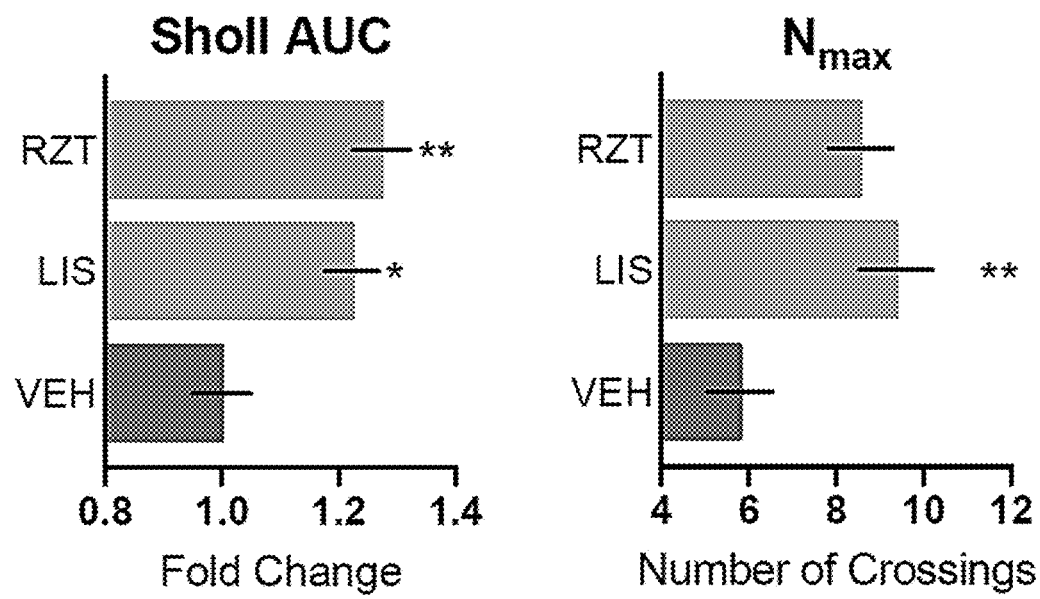
FIG. 1D shows area under the curve (AUC), maximum number of crossings ($N_{max}$), and number of branches determined from the Sholl plots, respectively.
Figure 1D:
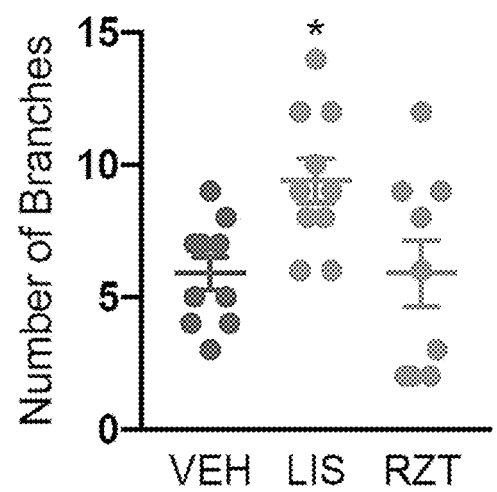

The present invention provides a method of using non-hallucinogenic analogs of psychedelic compounds for increasing neural plasticity of the neuronal cell. Several compounds have demonstrated to increase neuritogenesis and/or spinogenesis both in vitro and in vivo. These changes in neuronal structure are accompanied by increased synapse numbers and function as measured by fluorescence microscopy and electrophysiology. The non-hallucinogenic analogs of psychedelic compounds may improve mood by increasing translation of key neurotrophic factor proteins involved in neural plasticity. More importantly, by using non-hallucinogenic analogs of psychedelics, the plasticity-promoting properties of these compounds can be separated from their undesired hallucinogenic effect.

The present invention provides a method of using non-hallucinogenic analogs of psychedelic compounds for treatment of a brain disorder. The brain disorder can be a psychiatric disorder including depression, anxiety, and/or post-traumatic stress disorder. The brain disorder can be a substance use disorder. And the brain disorder can be a neurodegenerative disorder including Alzheimer's and/or Parkinson's diseases.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_1$-$C_2$, $C_1$-$C_3$, $C_1$-$C_4$, $C_1$-$C_5$, $C_1$-$C_6$, $C_1$-$C_7$, $C_1$-$C_8$, $C_1$-$C_9$, $C_1$-$C_{10}$, $C_2$-$C_3$, $C_2$-$C_4$, $C_2$-$C_5$, $C_2$-$C_6$, $C_3$-$C_4$, $C_3$-$C_5$, $C_3$-$C_6$, $C_4$-$C_5$, $C_4$-$C_6$ and $C_5$-$C_6$. For example, $C_1$-$C_6$ alkyl includes, but is not limited to, methyl, ethyl, propyl, isopropyl, butyl, isobutyl, sec.butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_2$-$C_3$, $C_2$-$C_4$, $C_2$-$C_5$, $C_2$-$C_6$, $C_2$-$C_7$, $C_2$-$C_8$, $C_2$-$C_9$, $C_2$-$C_{10}$, $C_3$, $C_3$-$C_4$, $C_3$-$C_5$, $C_3$-$C_6$, $C_4$, $C_4$-$C_5$, $C_4$-$C_5$, $C_5$, $C_5$-$C_6$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_3$-$C_6$, $C_4$-$C_6$, $C_5$-$C_6$, $C_3$-$C_8$, $C_4$-$C_8$, $C_5$-$C_8$, $C_6$-$C_8$, $C_3$-$C_9$, $C_3$-$C_{10}$, $C_3$-$C_{11}$, and $C_3$-$C_{12}$. Saturated monocyclic cycloalkyl rings include, for example, cyclopropyl, cyclobutyl, cyclopentyl, cyclohexyl, and cyclooctyl.

Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_3$-$C_8$ cycloalkyl, exemplary groups include, but are not limited to cyclopropyl, cyclobutyl, cyclopentyl, and cyclohexyl. Cycloalkyl groups can be substituted or unsubstituted.

"Alkoxy" refers to an alkyl group having an oxygen atom that connects the alkyl group to the point of attachment: alkyl-O—. As for the alkyl group, alkoxy groups can have any suitable number of carbon atoms, such as $C_1$-$C_6$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Hydroxyalkyl" or "alkylhydroxy" refer to an alkyl group, as defined above, where at least one of the hydrogen atoms is replaced with a hydroxy group. As for the alkyl group, alkylhydroxy groups can have any suitable number of carbon atoms, such as $C_1$-$C_6$. Exemplary alkylhydroxy groups include, but are not limited to, hydroxy-methyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Halogen" refers to fluorine, chlorine, bromine and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_1$-$C_6$. For example, haloalkyl includes trifluoromethyl, fluoromethyl, etc. In some instances, the term "perfluoro" can be used to define a compound or radical where all the hydrogens are replaced with fluorine. For example, perfluoromethane includes 1,1,1-trifluoromethyl.

"Amino" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), or secondary (one R is hydrogen) or tertiary (each R is other than hydrogen).

"Alkylamino" refers a secondary amino group where one R is hydrogen and the other R is alkyl, as defined above. As for the alkyl group, alkylamino groups can have any suitable number of carbon atoms, such as $C_1$-$C_6$. Alkylamino groups useful in the present invention include, but are not limited to, methylamino and ethylamino.

"Dialkylamino" refers a tertiary amino group where both R groups are alkyl, as defined above. As for the alkyl group, dialkylamino groups can have any suitable number of carbon atoms, such as $C_1$-$C_6$. Dialkylamino groups useful in the present invention include, but are not limited to, dimethylamino and diethylamino.

"Aminoalkyl" refers to alkyl, as defined above, where one or more hydrogen atoms are replaced with an amino group. As for the alkyl group, aminoalkyl groups can have any suitable number of carbon atoms, such as $C_1$-$C_6$. Aminoalkyl groups useful in the present invention include, but are not limited to, dimethylaminoethyl, dimethylaminopropyl, dimethylaminobutyl, and diethylaminopropyl.

"Heterocycloalkyl" refers to a saturated ring system having from 3 to 12 ring members and from 1 to 4 heteroatoms of N, O and S. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"N—($C_1$-$C_6$ alkyl)pyrrolidinyl" or "N—($C_1$-$C_6$ alkyl)piperidinyl" refers to pyrrolidinyl or piperidinyl group, where the nitrogen (N) of the pyrrolidinyl or piperidinyl group has an alkyl group, as defined above. The pyrrolidinyl can be 1-, 2- or 3-pyrrolidinyl, piperidinyl can be 1-, 2-, 3- or 4-piperidinyl. The N—($C_1$-$C_6$ alkyl)pyrrolidinyl groups useful in the present invention include, but are not limited to, N-methyl-2pyrrolidinyl. The N—($C_1$-$C_6$ alkyl)piperidinyl groups useful in the present invention include, but are not limited to, N-methyl-4-piperidinyl.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Hydrate" refers to a compound that is complexed to at least one water molecule. The compounds of the present invention can be complexed with from 1 to 10 water molecules.

"Isomers" refers to compounds with the same chemical formula but which are structurally distinguishable. Certain compounds of the present invention possess asymmetric carbon atoms (optical centers) or double bonds; the racemates, diastereomers, geometric isomers and individual isomers are all intended to be encompassed within the scope of the present invention.

"Tautomer" refers to one of two or more structural isomers which exist in equilibrium and which are readily converted from one form to another.

The present invention includes all tautomers and stereoisomers of compounds of the present invention, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

"Sholl analysis" is a method of quantitative analysis commonly used in neuronal studies to characterize the morphological characteristics of an imaged neuron. It creates a series of concentric circles around the soma of the neuron, and counts how many times the neuron intersects with the circumference of these circles. Common analysis methods include linear analysis, semi-log analysis, and log-log analysis.

The linear method is the analysis of the function N(r), where N is the number of crossings for a circle of radius r. The critical value is the radius r at which there is a maximum number of dendritic crossings, this value is closely related to the dendrite maximum ($N_{max}$). Dendrite maximum ($N_{max}$) is the maximum of the function N(r), as specified by the critical value for a given data set. Schoenen Ramification Index is one measure of the branching of the neuronal cell being studied. It is calculated by dividing the dendrite maximum by the number of primary dendrites, that is, the number of dendrites originating at the cell's soma.

"A Sholl plot" refers to a plot with the number of crossings (N) at the Y axis of the plot and the radius r of the circle at the X axis of the plot. The Sholl plot provides an area-under-curve (AUC).

From an imaged neuron, other parameters can also be obtained to measure arbor complexity, for example, a number of dendritic branches, a number of primary dendrites, a total dendritic length, and a length of longest dendrite.

"A number of dendritic branches" refers to the total number of branches per neuron.

"A number of primary dendrites" refers to the number of dendrites originating at the cell's soma.

"A total dendritic length" refers to the total length of all dendrites per neurons.

"A length of longest dendrite" refers to the length of the longest dendrite for a particular neuron.

A dendritic spine (or spine) is a small membranous protrusion from a neuron's dendrite that typically receives input from a single axon at the synapse. Dendritic spines serve as a storage site for synaptic strength and help transmit electrical signals to the neuron's cell body. Most spines have a bulbous head (the spine head), and a thin neck that connects the head of the spine to the shaft of the dendrite. Dendritic spines are small with spine head volumes ranging 0.01 $\mu m^3$ to 0.8 $\mu m^3$. Spines with strong synaptic contacts typically have a large spine head, which connects to the dendrite via a membranous neck. The most notable classes of spine shape are "thin", "filopodium", "stubby", and "mushroom".

"A density of dendritic spines" refers to numbers of spines per 10 μm (the length of dendrite).

Synapses is defined in the present invention as a colocalization of a presynaptic protein (VGLUT1 punta) and a post-synaptic protein (PSD-95 puncta). Also see Example 2.8.

"A density of synapse" refers to numbers of synapses per unit length (of the dendrite)

"Fold" refers to the fold ratio (also called fold change), and is the ratio of the measured value for an experimental sample to the measured value for the control sample. In the present invention, the measured value of a property of the neuronal cells treated with the non-hallucinogenic analog of a psychedelic compound (i.e., the compound) is compared to the one treated with a vehicle solution without the testing compound (i.e., the vehicle control). The ratio of the measured value of the neuronal cells treated with the compound to the vehicle control is determined by fold. The property of the neuronal cells includes, but is not limited to, a maximum number of dendritic crossings, an AUC, a number of dendritic branches, a number of primary dendrites, a total dendritic length, a length of longest dendrite, a density of dendritic spines, a density of synapse, a density of a presynaptic protein (e.g., VGLUT1), a density of a postsynaptic protein (e.g., PSD-95), a density of colocalization of presynaptic (e.g., VGLUT1) and postsynaptic (e.g., PSD-95), and translation, transcript, or secretion of neurotrophic factors (e.g., BDNF and GDNF).

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject in need thereof" refers to a living organism suffering from or prone to a condition that can be treated by administration of a pharmaceutical composition as provided herein. Non-limiting examples include humans, other mammals, for example primates cows, sheep, goats, horses, dogs, cats, rabbits, rats, mice and the like, and other non-mammalian animals.

"Disorder" or "condition" refer to a state of being or health status of a patient or subject capable of being treated with the non-hallucinogenic analog of a psychedelic compound of the present invention. Examples of disorders or conditions include, but are not limited to, a psychiatric disorder such as depression, anxiety, and post-traumatic stress disorder; a substance use disorder such as addition; and a neurodegenerative disorder such as Alzheimer's and Parkinson's diseases.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Methods of Increasing Neural Plasticity

In one aspect, provided herein is a method of increasing neural plasticity. The method includes contacting a neuronal cell with a non-hallucinogenic analog of a psychedelic compound, in an amount sufficient to increase neural plasticity of the neuronal cell, wherein the non-hallucinogenic analog of a psychedelic compound produces a maximum number of dendritic crossings with an increase of greater than 1.0 fold by a Sholl Analysis.

The neuronal cells can be any type of neuron cells. In some embodiments, the neuron cell is a cortical neuron cell. In some embodiments, the neuron cell is a cortical pyramidal neuron cell.

A. Determining Neural Plasticity Promoted by Non-Hallucinogenic Analogs of Psychedelic Compounds Neural plasticity refers to the ability of neurons to change in form and function in response to alterations in their environment. The neural plasticity can be evaluated by neuritogenesis, spinogenesis, and synaptogenesis in neurons. Neurogenesis is the formation of neurites. Spinogenesis is the development of dendritic spines in neurons. Synaptogenesis is the formation of synapses between neurons in the nervous system.

Neuritogenesis in Neurons

First, the non-hallucinogenic analog of a psychedelic compound (i.e., the compounds) promotes neuritogenesis in neuronal cells. A Sholl analysis can be used to study the neuritogenesis by evaluating, for example, a maximum number of dendritic crossings and an area-under-curve (AUC) of the Sholl plot. From an imaged neuron, neuritogenesis can also be evaluated by a number of dendritic branches, a number of primary dendrites, a total dendritic length, and a length of longest dendrite.

In some embodiments, the non-hallucinogenic analog of a psychedelic compound produces a maximum number of dendritic crossings with an increase of greater than 1.0 fold by the Sholl Analysis. In some embodiments, the non-hallucinogenic analog of a psychedelic compound produces a maximum number of dendritic crossings with an increase of greater than 1.2 fold, greater than 1.5 fold, or greater than 2.0 fold, by the Sholl Analysis. In other embodiments, the non-hallucinogenic analog of a psychedelic compound produces a maximum number of dendritic crossings with an increase of from 1.0 to 3.0 fold, from 1.0 to 2.5 fold, from 1.0 to 2.0 fold, from 1.0 to 1.5 fold, from 1.5 to 3.0 fold, from 1.2 to 2.5 fold, from 1.5 to 2.5 fold, from 1.2 to 2.0 fold, from 1.5 to 2.0 fold, or from 1.2 to 1.5 fold, by the Sholl Analysis.

The non-hallucinogenic analog of a psychedelic compound also has a similar effect on other morphologies of neurons, for example, an area-under-curve (AUC) of the Sholl plot, a number of dendritic branches, and a total dendritic length.

In some embodiments, the non-hallucinogenic analog of a psychedelic compound produces an area-under-curve (AUC) of the Sholl plot with an increase of greater than 1.0 fold by the Sholl Analysis.

In other embodiments, the non-hallucinogenic analog of a psychedelic compound produces an AUC of the Sholl plot with an increase of greater than 1.2 fold, greater than 1.5 fold, or greater than 2.0 fold. In still other embodiments, the non-hallucinogenic analog of a psychedelic compound produces the AUC of the Sholl plot with an increase of from 1.0 to 3.0 fold, from 1.0 to 2.5 fold, from 1.0 to 2.0 fold, from 1.0 to 1.5 fold, from 1.5 to 3.0 fold, from 1.2 to 2.5 fold, from 1.5 to 2.5 fold, from 1.2 to 2.0 fold, from 1.5 to 2.0 fold, or from 1.2 to 1.5 fold.

In some embodiments, the non-hallucinogenic analog of a psychedelic compound produces a number of dendritic branches with an increase of greater than 1.0 fold.

In other embodiments, the non-hallucinogenic analog of a psychedelic compound produces a number of dendritic branches with an increase of greater than 1.2 fold, greater than 1.5 fold, or greater than 2.0 fold. In still other embodiments, the non-hallucinogenic analog of a psychedelic compound produces a number of dendritic branches with an increase of from 1.0 to 3.0 fold, from 1.0 to 2.5 fold, from 1.0 to 2.0 fold, from 1.0 to 1.5 fold, from 1.5 to 3.0 fold, from 1.2 to 2.5 fold, from 1.5 to 2.5 fold, from 1.2 to 2.0 fold, from 1.5 to 2.0 fold, or from 1.2 to 1.5 fold.

In some embodiments, the non-hallucinogenic analog of a psychedelic compound produces a total dendritic length with an increase of greater than 1.0 fold.

In other embodiments, the non-hallucinogenic analog of a psychedelic compound produces a total dendritic length with an increase of greater than 1.2 fold, greater than 1.5 fold, or greater than 2.0 fold. In still other embodiments, the non-hallucinogenic analog of a psychedelic compound produces a total dendritic length with an increase of from 1.0 to 3.0 fold, from 1.0 to 2.5 fold, from 1.0 to 2.0 fold, from 1.0 to 1.5 fold, from 1.5 to 3.0 fold, from 1.2 to 2.5 fold, from 1.5 to 2.5 fold, from 1.2 to 2.0 fold, from 1.5 to 2.0 fold, or from 1.2 to 1.5 fold.

The non-hallucinogenic analog of a psychedelic compound may have a limited effect on a number of primary dendrites. In some embodiments, the non-hallucinogenic analog of a psychedelic compound produces a number of primary dendrites with an increase of greater than 1.0 fold. In other embodiments, the non-hallucinogenic analog of a psychedelic compound produces a number of primary dendrites at about 1.0 fold.

The non-hallucinogenic analog of a psychedelic compound may have a limited effect on a length of the longest dendrite. In some embodiments, the non-hallucinogenic analog of a psychedelic compound produces a length of the longest dendrite with an increase of greater than 1.0 fold. In other embodiments, the non-hallucinogenic analog of a psychedelic compound produces a length of the longest dendrite at about 1.0 fold.

The neuronal cells can be treated with various concentrations of the non-hallucinogenic analog of a psychedelic compound. In some embodiments, the neuronal cells are treated with the non-hallucinogenic analog of a psychedelic compound at a concentration of 90 $\mu$M, 10 $\mu$M, 100 nM, 1 nM, 10 pM, or 0.1 pM. In one specific embodiment, the neuronal cells are treated with the compound at a concentration of 90 $\mu$M. In another specific embodiment, the neuronal cells are treated with the compound at a concentration of 10 $\mu$M.

In some embodiments, the non-hallucinogenic analog of a psychedelic compound at a concentration of 10 $\mu$M produces a maximum number of dendritic crossings with an increase of greater than 1.0 fold by the Sholl Analysis. In some embodiments, the non-hallucinogenic analog of a psychedelic compound at a concentration of 100 nM produces a maximum number of dendritic crossings with an increase of greater than 1.0 fold by the Sholl Analysis. In other embodiments, the non-hallucinogenic analog of a psychedelic compound at a concentration of 1 nM produces a maximum number of dendritic crossings with an increase of greater than 1.0 fold by the Sholl Analysis. In other embodiments, the non-hallucinogenic analog of a psychedelic compound at a concentration of 10 pM produces a maximum number of dendritic crossings with an increase of greater than 1.0 fold by the Sholl Analysis. In still other embodiments, the non-hallucinogenic analog of a psychedelic compound at a concentration of 0.1 pM produces a maximum number of dendritic crossings with an increase of greater than 1.0 fold by the Sholl Analysis.

In some embodiments, the non-hallucinogenic analog of a psychedelic compound at a concentration of 10 µM produces an AUC of the Sholl plot with an increase of greater than 1.0 fold by the Sholl Analysis. In some embodiments, the non-hallucinogenic analog of a psychedelic compound at a concentration of 100 nM produces an AUC of the Sholl plot with an increase of greater than 1.0 fold by the Sholl Analysis. In other embodiments, the non-hallucinogenic analog of a psychedelic compound at a concentration of 1 nM produces an AUC of the Sholl plot with an increase of greater than 1.0 fold by the Sholl Analysis. In other embodiments, the non-hallucinogenic analog of a psychedelic compound at a concentration of 10 pM produces an AUC of the Sholl plot with an increase of greater than 1.0 fold by the Sholl Analysis. In still other embodiments, the non-hallucinogenic analog of a psychedelic compound at a concentration of 0.1 pM produces an AUC of the Sholl plot with an increase of greater than 1.0 fold by the Sholl Analysis.

In some embodiments, the non-hallucinogenic analog of a psychedelic compound at a concentration of 10 µM produces a number of dendritic branches with an increase of greater than 1.0 fold. In some embodiments, the non-hallucinogenic analog of a psychedelic compound at a concentration of 100 nM produces a number of dendritic branches with an increase of greater than 1.0 fold. In other embodiments, the non-hallucinogenic analog of a psychedelic compound at a concentration of 1 nM produces a number of dendritic branches with an increase of greater than 1.0 fold. In other embodiments, the non-hallucinogenic analog of a psychedelic compound at a concentration of 10 pM produces a number of dendritic branches with an increase of greater than 1.0 fold. In still other embodiments, the non-hallucinogenic analog of a psychedelic compound at a concentration of 0.1 pM produces a number of dendritic branches with an increase of greater than 1.0 fold.

In some embodiments, the non-hallucinogenic analog of a psychedelic compound at a concentration of 10 µM produces a total dendritic length with an increase of greater than 1.0 fold. In some embodiments, the non-hallucinogenic analog of a psychedelic compound at a concentration of 100 nM produces a total dendritic length with an increase of greater than 1.0 fold. In other embodiments, the non-hallucinogenic analog of a psychedelic compound at a concentration of 1 nM produces a total dendritic length with an increase of greater than 1.0 fold. In other embodiments, the non-hallucinogenic analog of a psychedelic compound at a concentration of 10 pM produces a total dendritic length with an increase of greater than 1.0 fold. In still other embodiments, the non-hallucinogenic analog of a psychedelic compound at a concentration of 0.1 pM produces a total dendritic length with an increase of greater than 1.0 fold.

The neuritogenesis, promoted by the non-hallucinogenic analog of a psychedelic compound, can be studied in vitro with neuronal cells as well as in vivo or ex vivo. For Example, Drosophila larvae during various instars or zebrafish embryos can be treated with the non-hallucinogenic analog of a psychedelic compound to assess the in vivo effects of the compound on neuritogenesis.

Spinogenesis in Neurons

Second, the non-hallucinogenic analog of a psychedelic compound promotes spinogenesis in neuronal cells. The spinogenesis can be evaluated by a density of dendritic spines, and further by a shift in spine morphology.

In some embodiments, the non-hallucinogenic analog of a psychedelic compound produces a density of dendritic spines with an increase of greater than 1.0 fold.

In other embodiments, the non-hallucinogenic analog of a psychedelic compound produces a density of dendritic spines with an increase of greater than 1.2 fold, greater than 1.5 fold, or greater than 2.0 fold. In still other embodiments, the non-hallucinogenic analog of a psychedelic compound produces a density of dendritic spines with an increase of from 1.0 to 3.0 fold, from 1.0 to 2.5 fold, from 1.0 to 2.0 fold, from 1.0 to 1.5 fold, from 1.5 to 3.0 fold, from 1.2 to 2.5 fold, from 1.5 to 2.5 fold, from 1.2 to 2.0 fold, from 1.5 to 2.0 fold, or from 1.2 to 1.5 fold.

Apart from the increase of the density of dendritic spines, the non-hallucinogenic analog of a psychedelic compound may also cause a shift in spine morphology, favoring immature (thin and filopodium) over more mature (mushroom) spine types.

The neuronal cells can be treated with various concentrations of the non-hallucinogenic analog of a psychedelic compound, as detailed above.

In some embodiments, the non-hallucinogenic analog of a psychedelic compound at a concentration of 10 µM produces a density of dendritic spines with an increase of greater than 1.0 fold. In some embodiments, the non-hallucinogenic analog of a psychedelic compound at a concentration of 100 nM produces a density of dendritic spines with an increase of greater than 1.0 fold. In other embodiments, the non-hallucinogenic analog of a psychedelic compound at a concentration of 1 nM produces a density of dendritic spines with an increase of greater than 1.0 fold. In other embodiments, the non-hallucinogenic analog of a psychedelic compound at a concentration of 10 pM produces a density of dendritic spines with an increase of greater than 1.0 fold. In still other embodiments, the non-hallucinogenic analog of a psychedelic compound at a concentration of 0.1 pM produces a density of dendritic spines with an increase of greater than 1.0 fold.

The spinogenesis, promoted by the non-hallucinogenic analog of a psychedelic compound, can be studied in vitro with neuronal cells as well as in vivo or Ex vivo. For Example, the effects of the compound on spinogenesis in the mPFC of adult rats using Golgi-Cox staining can be accessed.

It is also noted in in vivo studies that the non-hallucinogenic analog of a psychedelic compound promotes spinogenesis in pyramidal neurons with an increased density of dendritic spines of apical and/or basal dendrites. In some embodiments, the non-hallucinogenic analog of a psychedelic compound produces a density of dendritic spines of apical dendrites with an increase of greater than 1.0 fold. In some embodiments, the non-hallucinogenic analog of a psychedelic compound produces a density of dendritic spines of basal dendrites with an increase of greater than 1.0 fold. In some other embodiments, the non-hallucinogenic analog of a psychedelic compound produces a density of dendritic spines of both apical dendrites and basal dendrites with an increase of greater than 1.0 fold.

In addition to the structural changed in pyramidal neurons as described above, both the frequency and amplitude of spontaneous excitatory postsynaptic currents (EPSCs) can increase following the treatment of the compound.

Synaptogenesis in Neurons

Third, the non-hallucinogenic analog of a psychedelic compound promotes synaptogenesis in neuronal cells. The spinogenesis can be evaluated by a density of synapses (i.e., number of synapses per neuron) as well as the size of synapses.

In some embodiments, the non-hallucinogenic analog of a psychedelic compound produces a density of synapses with an increase of greater than 1.0 fold.

In other embodiments, the non-hallucinogenic analog of a psychedelic compound produces a density of synapses with an increase of greater than 1.2 fold, greater than 1.5 fold, or greater than 2.0 fold. In still other embodiments, the non-hallucinogenic analog of a psychedelic compound produces a density of synapse with an increase of from 1.0 to 3.0 fold, from 1.0 to 2.5 fold, from 1.0 to 2.0 fold, from 1.0 to 1.5 fold, from 1.5 to 3.0 fold, from 1.2 to 2.5 fold, from 1.5 to 2.5 fold, from 1.2 to 2.0 fold, from 1.5 to 2.0 fold, or from 1.2 to 1.5 fold.

The non-hallucinogenic analog of a psychedelic compound may have a limited effect on the size of synapses. In some embodiments, the non-hallucinogenic analog of a psychedelic compound produces a size of synapses at about 1.0 fold.

The increase of the density of synapses can lead to an increase of a density of a presynaptic protein such as vesicular glutamate transporter 1 (VGLUT1).

In some embodiments, the non-hallucinogenic analog of a psychedelic compound produces a density of a presynaptic protein with an increase of greater than 1.0 fold. In other embodiments, the non-hallucinogenic analog of a psychedelic compound produces a density of a presynaptic protein with an increase of greater than 1.2 fold, greater than 1.5 fold, or greater than 2.0 fold. In still other embodiments, the non-hallucinogenic analog of a psychedelic compound produces a density of a presynaptic protein with an increase of from 1.0 to 3.0 fold, from 1.0 to 2.5 fold, from 1.0 to 2.0 fold, from 1.0 to 1.5 fold, from 1.5 to 3.0 fold, from 1.2 to 2.5 fold, from 1.5 to 2.5 fold, from 1.2 to 2.0 fold, from 1.5 to 2.0 fold, or from 1.2 to 1.5 fold. The presynaptic protein is vesicular glutamate transporter 1 (VGLUT1).

The increase of the density of synapses may have a limited effect on a density of a postsynaptic protein such as postsynaptic density protein 95 (PSD-95). In some embodiments, the non-hallucinogenic analog of a psychedelic compound produces a density of a postsynaptic protein (PSD-95) at about 1.0 fold.

The neuronal cells can be treated with various concentrations of the non-hallucinogenic analog of a psychedelic compound, as detailed above.

In some embodiments, the non-hallucinogenic analog of a psychedelic compound at a concentration of 10 μM produces a density of synapses with an increase of greater than 1.0 fold.

In some embodiments, the non-hallucinogenic analog of a psychedelic compound at a concentration of 100 nM produces a density of synapses with an increase of greater than 1.0 fold.

In other embodiments, the non-hallucinogenic analog of a psychedelic compound at a concentration of 1 nM produces a density of synapses with an increase of greater than 1.0 fold.

In other embodiments, the non-hallucinogenic analog of a psychedelic compound at a concentration of 10 pM produces a density of synapses with an increase of greater than 1.0 fold.

In still other embodiments, the non-hallucinogenic analog of a psychedelic compound at a concentration of 0.1 pM produces a density of synapses with an increase of greater than 1.0 fold.

Translation, Transcript, and Secretion of Neurotrophic Factors

The role of brain-derived neurotrophic factor (BDNF) in both neuritogenesis and spinogenesis is well-known. See Cohen-Cory, et. al., *Dev. Neurobiol* 2010, 70, 271-288. The non-hallucinogenic analog of a psychedelic compound is evaluated for its effect on translation, transcript, or secretion of the neurotrophic factors in neuronal cells.

In some embodiments, the non-hallucinogenic analog of a psychedelic compound increases at least one of translation, transcription, and secretion of neurotrophic factors. The neurotrophic factor is at least one of a brain-derived neurotrophic factor (BDNF) and a glial cell line-derived neurotrophic factor (GDNF). In some embodiments, the neurotrophic factor is BDNF.

The non-hallucinogenic analog of a psychedelic compound increases translation of the brain-derived neurotrophic factor (BDNF). In some embodiments, the translation of the brain-derived neurotrophic factor (BDNF) has an increase of greater than 1.0 fold. In other embodiments, the translation of the brain-derived neurotrophic factor (BDNF) has an increase of greater than 1.2 fold, greater than 1.5 fold, or greater than 2.0 fold. In still other embodiments, the translation of the brain-derived neurotrophic factor (BDNF) has an increase of from 1.0 to 3.0 fold, from 1.0 to 2.5 fold, from 1.0 to 2.0 fold, from 1.0 to 1.5 fold, from 1.5 to 3.0 fold, from 1.2 to 2.5 fold, from 1.5 to 2.5 fold, from 1.2 to 2.0 fold, from 1.5 to 2.0 fold, or from 1.2 to 1.5 fold.

The non-hallucinogenic analog of a psychedelic compound increases translation of the glial cell line-derived neurotrophic factor (GDNF). In some embodiments, the translation of the glial cell line-derived neurotrophic factor (GDNF) has an increase of greater than 1.0 fold. In other embodiments, the translation of the glial cell line-derived neurotrophic factor (GDNF) has an increase of greater than 1.2 fold, greater than 1.5 fold, or greater than 2.0 fold. In still other embodiments, the translation of the glial cell line-derived neurotrophic factor (GDNF) has an increase of from 1.0 to 3.0 fold, from 1.0 to 2.5 fold, from 1.0 to 2.0 fold, from 1.0 to 1.5 fold, from 1.5 to 3.0 fold, from 1.2 to 2.5 fold, from 1.5 to 2.5 fold, from 1.2 to 2.0 fold, from 1.5 to 2.0 fold, or from 1.2 to 1.5 fold.

The non-hallucinogenic analog of a psychedelic compound has a minimal effect on transcript of the neurotrophic factors in neuronal cells. Therefore, the compound does not impact the neurotrophic factors at the level of gene expression.

B. Non-Hallucinogenic Analogs of Psychedelic Compounds

Neurotrophic factors are known to promote neuronal survival, neurogenesis, and neural plasticity and have been studied for treating neuropsychiatric and neurodegenerative disorders. However, these large water-soluble proteins do not readily cross the blood-brain barrier (BBB).

The non-hallucinogenic analogs of psychedelic compounds can have optimized physical properties giving them direct access to the brain. These compounds can increase endogenous brain levels of neurotrophic factors, thereby promoting neural plasticity in a brain region. Accordingly, in some embodiments, the non-hallucinogenic analog of a psychedelic compound is a blood-brain-barrier (BBB) penetrator.

Without being bound to a particular theory, the non-hallucinogenic analog of a psychedelic compound may have a novel "inside-out" mechanism by interacting with Sigma-1 receptors for their contribution to the beneficial effects of the compounds.

The non-hallucinogenic analogs of psychedelic compounds can be weak bases. As weak bases with pKa's of their conjugate acids falling within a narrow range of 7-10, these compounds can exist in both protonated and deprotonated states at physiological pH.

Accordingly, in some embodiments, the non-hallucinogenic analog of a psychedelic compound has a pKa of from 7.0 to 10.0.

In the deprotonated state, these compounds can readily cross cell membranes. However, their basicity causes them to accumulate in the acidic compartments of the secretory pathway. There, they can reach high local concentrations, bind to receptors (e.g., Sigma-1 receptors), and elicit effects. Accordingly, in some embodiments, the non-hallucinogenic analog of a psychedelic compound is permeable across cell membranes.

The non-hallucinogenic analog of a psychedelic compound can be an analog of ergolines or tryptamines. In some embodiments, the non-hallucinogenic analog of a psychedelic compound is an analog of ergolines. In other embodiments, the non-hallucinogenic analog of a psychedelic compound is an analog of tryptamines.

In some embodiments, the non-hallucinogenic analog of a psychedelic compound is a compound of Formula Ia or Ib:

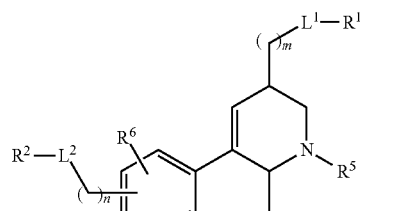

(Ia)

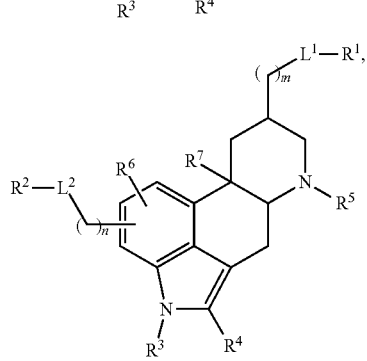

(Ib)

wherein:
L$^1$ is a bond, —C(O)NR$^a$—, —NR$^a$C(O)—, —NHC(O)NR$^a$—, —C(O)NR$^a$C(O)NH—, —C(O)O—, —OC(O)—, —NHC(O)O—, —SO$_2$NR$^a$—, —NHSO$_2$—, —SO$_2$—. —O—, —S—, or —NR$^a$—;

R$^1$ is hydrogen, C$_1$-C$_6$ alkyl, C$_2$-C$_6$ alkenyl, C$_3$-C$_8$ cycloalkyl, C$_1$-C$_6$ haloalkyl, C$_1$-C$_6$ hydroxyalkyl, C$_1$-C$_6$ alkoxy, C$_1$-C$_6$ aminoalkyl, aryl, heterocycloalkyl, or heteroaryl;

L$^2$ is a bond, —C(O)NR$^a$—, —NR$^a$C(O)—, —NHC(O)NR$^a$—, —C(O)O—, —OC(O)—, —NHC(O)O—, —SO$_2$NR$^a$—, —NHSO$_2$—, —SO$_2$—. —O—, —S—, or —NR$^a$—;

R$^2$ is hydrogen, halogen, —OH, C$_1$-C$_6$ alkyl, C$_2$-C$_6$ alkenyl, C$_3$-C$_8$ cycloalkyl, C$_1$-C$_6$ haloalkyl, C$_1$-C$_6$ hydroxyalkyl, C$_1$-C$_6$ alkoxy, C$_1$-C$_6$ aminoalkyl, aryl, heterocycloalkyl, or heteroaryl;

R$^a$ is hydrogen, C$_1$-C$_6$ alkyl, C$_2$-C$_6$ alkenyl, C$_3$-C$_8$ cycloalkyl, C$_1$-C$_6$ haloalkyl, C$_1$-C$_6$ hydroxyalkyl, C$_1$-C$_6$ alkoxy, or C$_1$-C$_6$ aminoalkyl;

R$^3$ is hydrogen, C$_1$-C$_6$ alkyl, or C$_2$-C$_6$ alkenyl;

R$^4$ is hydrogen, halogen, C$_1$-C$_6$ alkyl, C$_2$-C$_6$ alkenyl, or C$_1$-C$_6$ haloalkyl;

R$^5$ is C$_1$-C$_6$ alkyl or C$_2$-C$_6$ alkenyl;

R$^6$ is hydrogen, halogen, —OH, C$_1$-C$_6$ alkyl, C$_1$-C$_6$ haloalkyl, C$_1$-C$_6$ hydroxyalkyl, or C$_1$-C$_6$ alkoxy; and R$^7$ is hydrogen, —OH, C$_1$-C$_6$ alkyl, C$_1$-C$_6$ hydroxyalkyl, or C$_1$-C$_6$ alkoxy; and subscripts m and n are independently an integer from 0 to 3.

In some embodiments, L$^2$ is a bond, and subscript n is 0. In those embodiments, the non-hallucinogenic analog of a psychedelic compound is a compound of Formula Ia-1 or Ib-1:

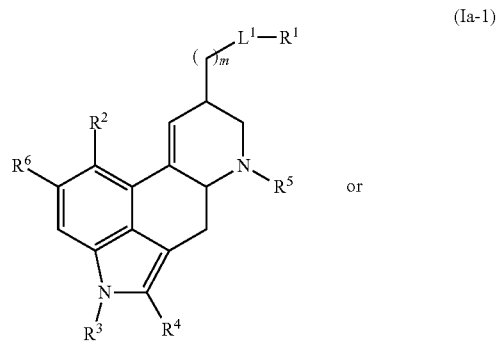

(Ia-1)

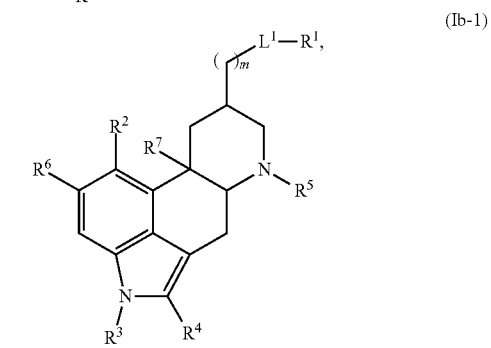

(Ib-1)

wherein:
L$^1$, R$^1$, R$^a$, R$^3$, R$^4$, R$^5$, R$^7$, and subscript m are as defined previously; and
each R$^2$ and R$^6$ is independently hydrogen, halogen, —OH, C$_1$-C$_6$ alkyl, C$_1$-C$_6$ haloalkyl, C$_1$-C$_6$ hydroxyalkyl, or C$_1$-C$_6$ alkoxy.

In some embodiments, each R$^2$ and R$^6$ is halogen, —OH, C$_1$-C$_6$ alkyl, C$_1$-C$_6$ haloalkyl, C$_1$-C$_6$ hydroxyalkyl, or C$_1$-C$_6$ alkoxy. Non-limiting examples of R$^2$ include —F, —OH, —CH$_3$, —CF$_3$, —CH$_2$OH, —OCH$_3$, and —OCH$_2$CH$_3$. Non-limiting examples of R$^6$ include —F, —OH, —CH$_3$, —CF$_3$, —CH$_2$OH, —OCH$_3$, and —OCH$_2$CH$_3$.

In other embodiments, each R$^2$ and R$^6$ is hydrogen. In those embodiments, the non-hallucinogenic analog of a psychedelic compound is a compound of Formula Ia-2 or Ib-2:

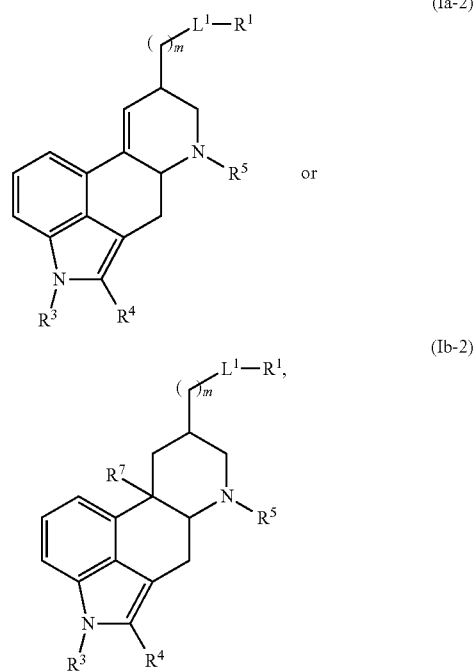

wherein L, R$^1$, R$^a$, R$^3$, R$^4$, R$^5$, R$^7$, and subscript m are as defined previously.

In some embodiments, L$^1$ is —C(O)NH—, —NHC(O)N(CH$_2$CH$_3$)—, —C(O)NR$^a$C(O)NH—, —C(O)O—, or —S—, wherein R$^a$ is dimethylaminopropyl. In some embodiments, L$^1$ is —C(O)NH—. In some specific embodiments, L$^1$ is —NHC(O)N(CH$_2$CH$_3$)—. In other specific embodiments, L$^1$ is —OC(O)—. In other specific embodiments, L$^1$ is —S—. In still other specific embodiments, L$^1$ is —C(O)N(CH$_2$CH$_2$CH$_2$N(CH$_3$)$_2$)C(O)NH—.

In some embodiments, R$^1$ is C$_1$-C$_6$ alkyl, C$_1$-C$_6$ hydroxyalkyl, heterocycloalkyl, or a N-containing heteroaryl.

R$^1$ can be C$_1$-C$_6$ alkyl. Non-limiting examples of C$_1$-C$_6$ alkyl include methyl, ethyl, propyl, and isopropyl. In some specific embodiments, R$^1$ is methyl. In other specific embodiments, R$^1$ is ethyl.

R$^1$ can be C$_1$-C$_6$ hydroxyalkyl. Non-limiting examples of C$_1$-C$_6$ hydroxyalkyl include —CH$_2$OH, —(CH$_2$)$_2$OH, —(CH$_2$)$_3$OH, —CH(CH$_3$)(CH$_2$OH), and —CH(CH$_2$CH$_3$)(CH$_2$OH). In some specific embodiments, R$^1$ is —CH(CH$_3$)(CH$_2$OH). In other specific embodiments, R$^1$ is —CH(CH$_2$CH$_3$)(CH$_2$OH).

R$^1$ can be a N-containing heteroaryl. Non-limiting examples of the N-containing heteroaryl include 2-pyridinyl, 3-pyridinyl, and 4-pyridinyl, each of which can be substituted with halogen. In some embodiments, R$^1$ is 5-bromo-3-pyridinyl.

R$^1$ can be heterocycloalkyl. In some specific embodiments, R$^1$ is

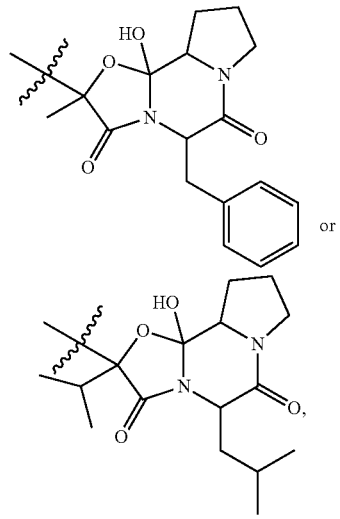

wherein the wavy line is the attachment to remainder of L.

In some embodiments, R$^3$ is hydrogen or C$_1$-C$_6$ alkyl. In some specific embodiments, R$^3$ is hydrogen. R$^3$ can be C$_1$-C$_6$ alkyl. Non-limiting examples of C$_1$-C$_6$ alkyl include methyl, ethyl and propyl. In other specific embodiments, R$^3$ is methyl.

In some embodiments, R$^4$ is hydrogen, halogen, and C$_1$-C$_6$ alkyl. In some specific embodiments, R$^4$ is hydrogen. R$^4$ can be halogen. Non-limiting examples of halogen include —Cl, —Br, and —F. In some specific embodiments, R$^4$ is —Br.

In some embodiments, R$^5$ is C$_1$-C$_6$ alkyl. Non-limiting examples of C$_1$-C$_6$ alkyl include methyl, ethyl, and propyl. In some specific embodiments, R$^5$ is methyl. In some specific embodiments, R$^5$ is ethyl. In other specific embodiments, R$^5$ is propyl.

In some embodiments, R$^5$ is C$_2$-C$_6$ alkenyl. Non-limiting examples of C$_2$-C$_6$ alkenyl include vinyl (ethenyl), propenyl, isopropenyl, 1-butenyl, 2-butenyl, and isobutenyl. In some specific embodiments, R$^5$ is propenyl.

In some embodiments, R$^7$ is hydrogen, —OH, or C$_1$-C$_6$ alkoxy. In some specific embodiments, R$^7$ is hydrogen. In other specific embodiments, R$^7$ is —OH. R$^7$ can be C$_1$-C$_6$ alkoxy. Non-limiting examples of C$_1$-C$_6$ alkoxy include methoxy, ethoxy, and propoxy. In some specific embodiments, R$^7$ is methoxy.

In some embodiments, subscript m is 0 or 1. In some specific embodiments, subscript m is 0. In other specific embodiments, subscript m is 1.

In more specific embodiments, the non-hallucinogenic analog of a psychedelic compound includes Ergometrine, Dihydroergotamine, Methylergometrine, Methysergide, Ergotamine, Cabergoline, Pergolide, Lisuride, 2-Bromo-lysergic acid diethylamide (BOL-148), Nicergoline, Bromocriptine, or combinations thereof.

In one embodiment, the non-hallucinogenic analog of a psychedelic compound is Ergometrine. In one embodiment, the non-hallucinogenic analog of a psychedelic compound is Dihydroergotamine. In one embodiment, the non-hallucinogenic analog of a psychedelic compound is Methylergometrine. In one embodiment, the non-hallucinogenic analog of a psychedelic compound is Methysergide. In another embodiment, the non-hallucinogenic analog of a psychedelic compound is Ergotamine. In another embodiment, the non-hallucinogenic analog of a psychedelic compound is Cabergoline. In another embodiment, the non-hallucinogenic analog of a psychedelic compound is Pergolide. In still another embodiment, the non-hallucinogenic analog of a psychedelic compound is Lisuride. In still another embodiment, the non-hallucinogenic analog of a psychedelic compound is 2-Bromo-lysergic acid diethylamide (BOL-148). In yet another embodiment, the non-hallucinogenic analog of a psychedelic compound is Nicergoline. In yet another embodiment, the non-hallucinogenic analog of a psychedelic compound is Bromocriptine.

In other embodiments, the non-hallucinogenic analog of a psychedelic compound is a compound of Formula IIa or IIb:

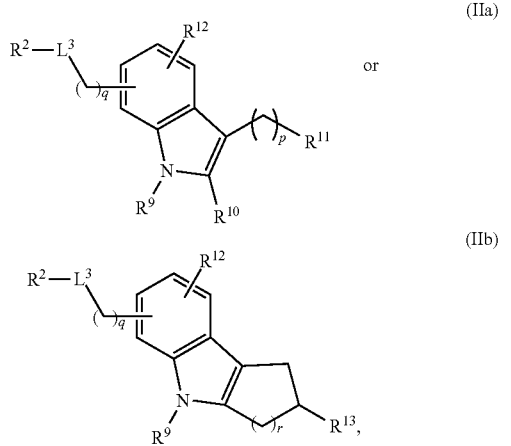

wherein:

$L^3$ is a bond, —C(O)NR$^b$—, —NR$^b$C(O)—, —NHC(O)NR$^b$—, —C(O)O—, —OC(O)—, —NHC(O)O—, —SO$_2$NR$^b$—, —NHSO$_2$—, —SO$_2$—, —O—, —S—, or —NR$^b$—;

$R^8$ is hydrogen, halogen, $C_1$-$C_6$ alkyl, $C_2$-$C_6$ alkenyl, $C_3$-$C_8$ cycloalkyl, $C_1$-$C_6$ haloalkyl, $C_1$-$C_6$ hydroxyalkyl, $C_1$-$C_6$ alkoxy, $C_1$-$C_6$ aminoalkyl, heterocycloalkyl, aryl, or heteroaryl;

$R^b$ is hydrogen, $C_1$-$C_6$ alkyl, $C_2$-$C_6$ alkenyl, $C_3$-$C_8$ cycloalkyl, $C_1$-$C_6$ haloalkyl, $C_1$-$C_6$ hydroxyalkyl, or $C_1$-$C_6$ alkoxy;

$R^9$ is hydrogen, $C_1$-$C_6$ alkyl, or $C_2$-$C_6$ alkenyl;

$R^{10}$ is hydrogen, halogen, $C_1$-$C_6$ alkyl, $C_2$-$C_6$ alkenyl, or $C_1$-$C_6$ haloalkyl;

$R^{11}$ is $C_1$-$C_6$ alkylamino, di-($C_1$-$C_6$ alkyl)amino, N—($C_1$-$C_6$ alkyl)pyrrolidinyl, or N—($C_1$-$C_6$ alkyl)piperidinyl;

$R^{12}$ is hydrogen, halogen, —OH, $C_1$-$C_6$ alkyl, $C_1$-$C_6$ haloalkyl, $C_1$-$C_6$ hydroxyalkyl, or $C_1$-$C_6$ alkoxy;

$R^{13}$ is $C_1$-$C_6$ alkylamino or di-($C_1$-$C_6$ alkyl)amino;

subscript p is an integer from 0 to 3;

subscript q is an integer from 0 to 3; and subscript r is an integer from 1 to 3.

In some embodiments, each of $R^9$ and $R^{10}$ is hydrogen. In those embodiments, the non-hallucinogenic analog of a psychedelic compound is a compound of Formula IIa-1 or IIb-1:

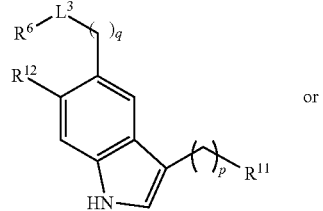

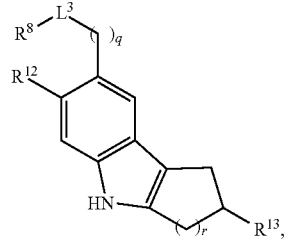

wherein $L^3$, $R^8$, $R^b$, $R^{11}$, $R^{12}$, $R^{13}$, subscripts q, p, and r are defined previously.

In some embodiments, $L^3$ is a bond, —C(O)NH—, —SO$_2$NH—, and —SO$_2$—. In some specific embodiments, $L^3$ is a bond. In some specific embodiments, $L^3$ is —C(O)NH—. In other specific embodiments, $L^3$ is —SO$_2$NH—. In other specific embodiments, $L^3$ is —SO$_2$—.

In some embodiments, $R^8$ is hydrogen, $C_1$-$C_6$ alkyl, heterocycloalkyl, aryl, or heteroaryl.

$R^8$ can be hydrogen or $C_1$-$C_6$ alkyl. In some specific embodiments, $R^8$ is hydrogen.

Non-limiting examples of $C_1$-$C_6$ alkyl include methyl, ethyl and propyl. In some specific embodiments, $R^8$ is methyl.

$R^8$ can be heterocycloalkyl. Non-limiting examples of heterocycloalkyl include pyrrolidine, piperidine, tetrahydrofuran, tetrahydrothiophene, pyrazolidine, imidazolidine, piperazine, oxazolidine, isoxazolidine, thiazolidine, isothiazolidine, and morpholine. In some specific embodiments, $R^8$ is

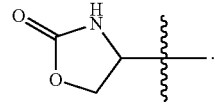

In other specific embodiments, $R^8$ is 1-pyrrolidinyl. In other specific embodiments, $R^8$ is 1-piperidinyl.

$R^8$ can be aryl. Non-limiting examples of aryl include phenyl, naphthyl and biphenyl.

In some specific embodiments, $R^8$ is phenyl.

$R^8$ can be heteroaryl. Non-limiting examples of heteroaryl include pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. In some specific embodiments, $R^8$ is triazolyl. In more specific embodiments, $R^8$ is 1,2,4-triazolyl.

In some embodiments, $R^{11}$ is di-($C_1$-$C_6$ alkyl)amino, N—($C_1$-$C_6$ alkyl)pyrrolidinyl, or N—($C_1$-$C_6$ alkyl)piperidinyl.

$R^{11}$ can be di-($C_1$-$C_6$ alkyl)amino. Non-limiting examples of di-($C_1$-$C_6$ alkyl)amino include —N(CH$_3$)$_2$, —N(CH$_2$CH$_3$)$_2$, —N(CH$_3$)(CH$_2$CH$_3$), and —N(CH$_2$CH$_2$CH$_3$)$_2$. In some specific embodiments, R$^{11}$ is —N(CH$_3$)$_2$.

R$^{11}$ can be N—(C$_1$-C$_6$ alkyl)pyrrolidinyl. Non-limiting examples of N—(C$_1$-C$_6$ alkyl)pyrrolidinyl include N-methylpyrrolidinyl. In some specific embodiments, R$^1$ is N-methyl-2-pyrrolidinyl.

R$^{11}$ can be N—(C$_1$-C$_6$ alkyl)piperidinyl. Non-limiting examples of N—(C$_1$-C$_6$ alkyl)piperidinyl include N-methylpiperidinyl. In some specific embodiments, R$^{11}$ is N-methyl-4-piperidinyl.

In some embodiments, R$^{12}$ is hydrogen, halogen, —OH, C$_1$-C$_6$ hydroxyalkyl, or C$_1$-C$_6$ alkoxy. In some specific embodiments, R$^{12}$ is hydrogen. R$^{12}$ can be halogen including —Cl, Br, or —F. In some specific embodiments, R$^{12}$ is —F. R$^{12}$ can be C$_1$-C$_6$ alkoxy including methoxy or ethoxy. In some specific embodiments, R$^{12}$ is methoxy.

In some embodiments, R$^{13}$ is C$_1$-C$_6$ alkylamino or di-(C$_1$-C$_6$ alkyl)amino. R$^{13}$ can be C$_1$-C$_6$ alkylamino. Non-limiting examples of C$_1$-C$_6$ alkylamino include —NHCH$_3$, —NHCH$_2$CH$_3$, and —NH(CH$_2$)$_2$CH$_3$. R$^{13}$ can be di-(C$_1$-C$_6$ alkyl)amino. Non-limiting examples of di-(C$_1$-C$_6$ alkyl) amino include —N(CH$_3$)$_2$, —N(CH$_2$CH$_3$)$_2$, —N(CH$_3$)(CH$_2$CH$_3$), and —N(CH$_2$CH$_2$CH$_3$)$_2$. In some specific embodiments, R$^{13}$ is —NHCH$_3$.

In some embodiments, subscript p is an integer from 0 to 2. In some specific embodiments, subscript p is 0. In some specific embodiments, subscript p is 1. In other specific embodiments, subscript p is 2.

In some embodiments, subscript q is an integer from 0 to 2. In some specific embodiments, subscript q is 0. In some specific embodiments, subscript q is 1. In other specific embodiments, subscript q is 2.

In some embodiments, subscript r is 1 or 2. In some specific embodiments, subscript r is 2.

In more specific embodiments, the non-hallucinogenic analog of a psychedelic compound includes Sumatriptan, Zolmitriptan, Rizatriptan, Eletriptan, Naratriptan, Frovatriptan, Almotriptan, 6-methoxy-N,N-dimethyltryptamine, 6-fluoro-N,N-dimethyltryptamine, or combinations thereof.

In one embodiment, the non-hallucinogenic analog of a psychedelic compound is Sumatriptan. In one embodiment, the non-hallucinogenic analog of a psychedelic compound is Zolmitriptan. In one embodiment, the non-hallucinogenic analog of a psychedelic compound is Rizatriptan. In one embodiment, the non-hallucinogenic analog of a psychedelic compound is Eletriptan. In another embodiment, the non-hallucinogenic analog of a psychedelic compound is Naratriptan. In another embodiment, the non-hallucinogenic analog of a psychedelic compound is Frovatriptan. In still another embodiment, the non-hallucinogenic analog of a psychedelic compound is Almotriptan. In still another embodiment, the non-hallucinogenic analog of a psychedelic compound is 6-methoxy-N,N-dimethyltryptamine. In yet another embodiment, the non-hallucinogenic analog of a psychedelic compound is 6-fluoro-N,N-dimethyltryptamine.

The compounds of the present invention can also be the salts and isomers thereof. In some embodiments, the compounds of the present invention include the salt forms thereof. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. These salts may be prepared by methods known to those skilled in art. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain basic acidic functionalities that allow the compounds to be converted into base addition salts. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2$H), tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see *Comprehensive Organic Transformations* Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention. Although some compounds described may indicate relative stereochemistry, the compounds may exist as a racemic mixture or as either enantiomer.

C. Determining Hallucinogenic Activity of Compounds

In general, animal behavior models are used to evaluate if the analogs of a psychedelic compound are non-hallucinogenic. See Hanks et. al., *Chemical Neuroscience* 2013, 4, 33-42 and Gonzalez-Maeso et. al., *Neuron* 2007, 53, 439-452. Hanks et. al. describes several animal behavior models including drug-induced head-twitch behavior and drug discrimination.

As described in detail in *J. Neurosci.*, 2003, 23(26), 8836-8843, Gonzalez-Maeso et. al. discloses that the non-hallucinogenic analog (i.e., Lisuride) causes no change of head-twitch response in the drug-induced head-twitch behavior models in mice. Accordingly, in some embodiments, the non-hallucinogenic analog of a psychedelic compound is evaluated by a drug-induced head-twitch behavior model.

The non-hallucinogenic analog of a psychedelic compound can also be evaluated using a drug discrimination behavior model. This animal behavior model is described in detail in Appel et. al. *Neuroscience & Biobehavioral Reviews*, Vol 6, pp. 529-536, 1982.

The non-hallucinogenic analog of a psychedelic compound may be evaluated by in vitro methods. The distinct gene expression patterns induced by non-hallucinogenic and hallucinogenic compounds may be used to assess the hallucinogenic activity of compounds.

Also see Gonzalez-Maeso et. al., *Neuron* 2007, 53, 439-452. A FRET or BRET based assay used to detect the formation of the 5HT2A/mGlu2 dimer may also be used to assess the hallucinogenic activity of compounds. See Gonzalez-Maeso et. al. *Nature* 2008, Vol 452, page. 93-99.

IV. Pharmaceutical Compositions

In some embodiments, the present invention provides a pharmaceutical composition including a pharmaceutically acceptable excipient and a non-hallucinogenic analog of a psychedelic compound of the present invention.

In some embodiments of the pharmaceutical compositions, the non-hallucinogenic analog of a psychedelic compound, or a pharmaceutically acceptable salt thereof, is included in a therapeutically effective amount.

In some embodiments of the pharmaceutical compositions, the non-hallucinogenic analog of a psychedelic compound is a compound of Formula Ia or Ib, or a pharmaceutically salt thereof. In some embodiments of the pharmaceutical compositions, the non-hallucinogenic analog of a psychedelic compound is a compound of Formula Ia, or a pharmaceutically salt thereof. In some embodiments of the pharmaceutical compositions, the non-hallucinogenic analog of a psychedelic compound is a compound of Formula Ib, or a pharmaceutically salt thereof.

In some embodiments of the pharmaceutical compositions, the non-hallucinogenic analog of a psychedelic compound is a compound of Formula IIa or IIb, or a pharmaceutically salt thereof. In some embodiments of the pharmaceutical compositions, the non-hallucinogenic analog of a psychedelic compound is a compound of Formula IIa, or a pharmaceutically salt thereof. In some embodiments of the pharmaceutical compositions, the non-hallucinogenic analog of a psychedelic compound is a compound of Formula IIb, or a pharmaceutically salt thereof.

In some embodiments of the pharmaceutical compositions, the non-hallucinogenic analog of a psychedelic compound includes Ergometrine, Dihydroergotamine, Methylergometrine, Methysergide, Ergotamine, Cabergoline, Pergolide, Lisuride, 2-Bromo-lysergic acid diethylamide (BOL-148), Nicergoline, Bromocriptine, or combinations thereof.

In other embodiments of the pharmaceutical compositions, the non-hallucinogenic analog of a psychedelic compound includes Sumatriptan, Zolmitriptan, Rizatriptan, Eletriptan, Naratriptan, Frovatriptan, Almotriptan, 6-methoxy-N,N-dimethyltryptamine, 6-fluoro-N,N-dimethyltryptamine, or combination thereof.

In some embodiments of the pharmaceutical compositions, the pharmaceutical composition includes a second agent (e.g. therapeutic agent). In some embodiments of the pharmaceutical compositions, the pharmaceutical composition includes a second agent (e.g. therapeutic agent) in a therapeutically effective amount. In some embodiments of the pharmaceutical compositions, the second agent is an agent for treating a brain disorder. In some embodiments, the second agent is an anti-psychiatric disorder agent. In other embodiments, the second agent is an anti-substance use disorder agent. In other embodiments, the second agent is an anti-neurodegenerative agent.

V. Formulations

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, and a coloring agent.

The compositions of the present invention can also be delivered as microspheres for slow release in the body. For example, microspheres can be formulated for administration via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

VI. Administration

The compounds and compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds and compositions of the present invention, and any other agents, can be present in any suitable amount, and can depend on various factors including, but not limited to, weight and age of the subject, state of the disease, etc. Suitable dosage ranges include from about 0.1 mg to about 10,000 mg, or about 1 mg to about 1000 mg, or about 10 mg to about 750 mg, or about 25 mg to about 500 mg, or about 50 mg to about 250 mg. Suitable dosages also include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in increasing neural plasticity, or with adjunctive agents that may not be effective alone, but may contribute to the efficacy of the active agent.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

VII. Methods of Treating a Disorder

In one aspect, provided herein is a method of treating a brain disorder. The method includes administering to a subject in need thereof a therapeutically effective amount of a non-hallucinogenic analog of a psychedelic compound, thereby treating the brain disorder, wherein the non-hallucinogenic analog of a psychedelic compound increases neural plasticity of the neuronal cell; provided that the subject is not already being treated with one or more of the following:

Ergometrine for postpartum hemorrhage and postabortion hemorrhage due to uterine atony;
Dihydroergotamine for migraines or cluster headaches;
Methylergometrine for routine management after delivery of the placenta, postpartum atony and hemorrhage, subinvolution, or migraines;
Methysergide for migraines or cluster headaches;
Ergotamine for migraines or cluster headaches;
Cabergoline for hyperprolactinemic disorders or Parkinson's disease;
Pergolide for Parkinson's disease;
Lisuride for Parkinson's disease;
Nicergoline for senile dementia or other disorders with vascular origins;
Bromocriptine for pituitary tumors, Parkinson's disease, hyperprolactinaemia, neuroleptic malignant syndrome, or type 2 diabetes; or
Sumatriptan, Zolmitriptan, Rizatriptan, Eletriptan, Naratriptan, Frovatriptan, or Almotriptan for migraines or cluster headaches.

In some aspects, the method includes administering to a subject in need thereof a therapeutically effective amount of a non-hallucinogenic analog of a psychedelic compound, thereby treating the brain disorder, wherein the non-hallucinogenic analog of a psychedelic compound increases neural plasticity of the neuronal cell.

In other aspects, the method includes administering to a subject in need thereof a therapeutically effective amount of a non-hallucinogenic analog of a psychedelic compound, thereby treating the brain disorder, wherein the non-hallucinogenic analog of a psychedelic compound increases neural plasticity of the neuronal cell; provided that the subject is not already being treated with all of the following:

Ergometrine for postpartum hemorrhage and postabortion hemorrhage due to uterine atony;
Dihydroergotamine for migraines or cluster headaches;
Methylergometrine for routine management after delivery of the placenta, postpartum atony and hemorrhage, subinvolution, or migraines;
Methysergide for migraines or cluster headaches;
Ergotamine for migraines or cluster headaches;
Cabergoline for hyperprolactinemic disorders or Parkinson's disease;
Pergolide for Parkinson's disease;
Lisuride for Parkinson's disease;
Nicergoline for senile dementia or other disorders with vascular origins;
Bromocriptine for pituitary tumors, Parkinson's disease, hyperprolactinaemia, neuroleptic malignant syndrome, or type 2 diabetes; and
Sumatriptan, Zolmitriptan, Rizatriptan, Eletriptan, Naratriptan, Frovatriptan, or Almotriptan for migraines or cluster headaches.

In some embodiments, the non-hallucinogenic analog of a psychedelic compound, a pharmaceutically acceptable salt thereof, or a pharmaceutical composition thereof is included in a therapeutically effective amount.

In some embodiments, the brain disorder is a psychiatric disorder including depression, anxiety, and/or post-traumatic stress disorder. In those embodiments, the method of treating the psychiatric disorder includes administering to a subject in need thereof a therapeutically effective amount of a non-hallucinogenic analog of a psychedelic compound, a pharmaceutically acceptable salt thereof, or a pharmaceutical composition thereof. In some embodiments, the brain disorder is depression. In some embodiments, the brain disorder is anxiety. In other embodiments, the brain disorder is post-traumatic stress disorder.

The psychiatric disorder is a behavioral or mental pattern that may cause suffering or a poor ability to function in life. Such features may be persistent, relapsing and remitting, or occur as a single episode.

Depression is related to a mood disorder involving unusually intense and sustained sadness, melancholia, or despair. Anxiety or fear that interferes with normal functioning may be classified as an anxiety disorder. Commonly recognized categories include specific phobias, generalized anxiety disorder, social anxiety disorder, panic disorder, agoraphobia, obsessive-compulsive disorder and post-traumatic stress disorder.

In some embodiments, the brain disorder is a substance use disorder. In those embodiments, the method of treating the substance use disorder includes administering to a subject in need thereof a therapeutically effective amount of a non-hallucinogenic analog of a psychedelic compound, a pharmaceutically acceptable salt thereof, or a pharmaceutical composition thereof.

Substance use disorder (SUD), also known as drug use disorder, is a condition in which the use of one or more substances leads to a clinically significant impairment or distress. The term "substance" in this context is limited to psychoactive drugs. Addiction and dependence are components of a substance use disorder and addiction represents the most severe form of the disorder.

In other embodiments, the brain disorder is a neurodegenerative disorder including Alzheimer's and/or Parkinson's diseases. In those embodiments, the method of treating the neurodegenerative disorder includes administering to a subject in need thereof a therapeutically effective amount of a non-hallucinogenic analog of a psychedelic compound, a pharmaceutically acceptable salt thereof, or a pharmaceutical composition thereof. In some embodiments, the brain disorder is Alzheimer's disease. In other embodiments, the brain disorder is Parkinson's diseases.

Neurodegeneration is the progressive loss of structure or function of neurons, including death of neurons. Many neurodegenerative diseases including amyotrophic lateral sclerosis, Parkinson's, Alzheimer's, and Huntington's occur as a result of neurodegenerative processes.

The subject can be a living organism suffering from a brain disorder that can be treated by administration of a non-hallucinogenic analog of a psychedelic compound, a pharmaceutically acceptable salt thereof, or a pharmaceutical composition thereof. Non-limiting examples of the living organism include humans, other mammals, for example primates, cows, sheep, goats, horses, dogs, cats, rabbits, rats, mice and the like, and other non-mammalian animals. In some embodiments, the subject is a human. In some embodiments, the subject is an animal including a primate, a cow, a sheep, a goat, a horse, a dog, a cat, a rabbit, a rat, or a mice. In some specific embodiments, the subject is a horse. In some specific embodiments, the subject is a dog. In other specific embodiments, the subject is a cat.

The brain disorder in horses, dogs, or cats can be a psychiatric disorder including depression, anxiety, and/or post-traumatic stress disorder. In these embodiments, the method of treating the psychiatric disorder includes administering to a horse, a dog, or a cat in need thereof a therapeutically effective amount of a non-hallucinogenic analog of a psychedelic compound, a pharmaceutically acceptable salt thereof, or a pharmaceutical composition thereof. In some embodiments, the brain disorder is depression. In some embodiments, the brain disorder is anxiety. In other embodiments, the brain disorder is post-traumatic stress disorder.

In some embodiments, the non-hallucinogenic analog of a psychedelic compound is a compound of Formula Ia or Ib. In those embodiments, the method includes administering to a subject in need thereof a therapeutically effective amount of the non-hallucinogenic analog of a psychedelic compound having Formula Ia or Ib, a pharmaceutically acceptable salt thereof, or a pharmaceutical composition thereof. In some embodiments, the method includes administering to a subject in need thereof a therapeutically effective amount of the non-hallucinogenic analog of a psychedelic compound having Formula Ia, a pharmaceutically acceptable salt thereof, or a pharmaceutical composition thereof. In some embodiments, the method includes administering to a subject in need thereof a therapeutically effective amount of the non-hallucinogenic analog of a psychedelic compound having Formula Ib, a pharmaceutically acceptable salt thereof, or a pharmaceutical composition thereof.

In other embodiments, the non-hallucinogenic analog of a psychedelic compound is a compound of Formula IIa or IIb. In those embodiments, the method includes administering to a subject in need thereof a therapeutically effective amount of the non-hallucinogenic analog of a psychedelic compound having Formula IIa or IIb, a pharmaceutically acceptable salt thereof, or a pharmaceutical composition thereof. In other embodiments, the method includes administering to a subject in need thereof a therapeutically effective amount of the non-hallucinogenic analog of a psychedelic compound having Formula IIa, a pharmaceutically acceptable salt thereof, or a pharmaceutical composition thereof. In other embodiments, the method includes administering to a subject in need thereof a therapeutically effective amount of the non-hallucinogenic analog of a psychedelic compound having Formula IIb, a pharmaceutically acceptable salt thereof, or a pharmaceutical composition thereof.

In some embodiments, the non-hallucinogenic analog of a psychedelic compound includes Ergometrine, Dihydroergotamine, Methylergometrine, Methysergide, Ergotamine, Cabergoline, Pergolide, Lisuride, 2-Bromo-lysergic acid diethylamide (BOL-148), Nicergoline, Bromocriptine, or combinations thereof. In those embodiments, the method includes administering to a subject in need thereof a therapeutically effective amount of the non-hallucinogenic analog of a psychedelic compound including Ergometrine, Dihydroergotamine, Methylergometrine, Methysergide, Ergotamine, Cabergoline, Pergolide, Lisuride, 2-Bromo-lysergic acid diethylamide (BOL-148), Nicergoline, Bromocriptine, combinations thereof, a pharmaceutically acceptable salt thereof, or a pharmaceutical composition thereof.

In some embodiments, the method includes administering to a subject in need thereof a therapeutically effective amount of Ergometrine, a pharmaceutically acceptable salt thereof, or a pharmaceutical composition thereof. In some embodiments, the method includes administering to a subject in need thereof a therapeutically effective amount of Dihydroergotamine, a pharmaceutically acceptable salt thereof, or a pharmaceutical composition thereof. In some embodiments, the method includes administering to a subject in need thereof a therapeutically effective amount of Methylergometrine, a pharmaceutically acceptable salt thereof, or a pharmaceutical composition thereof. In some embodiments, the method includes administering to a subject in need thereof a therapeutically effective amount of Methysergide, a pharmaceutically acceptable salt thereof, or a pharmaceutical composition thereof. In other embodiments, the method includes administering to a subject in need thereof a therapeutically effective amount of Ergotamine, a pharmaceutically acceptable salt thereof, or a pharmaceutical composition thereof. In other embodiments, the method includes administering to a subject in need thereof a therapeutically effective amount of Cabergoline, a pharmaceutically acceptable salt thereof, or a pharmaceutical composition thereof. In other embodiments, the method includes administering to a subject in need thereof a therapeutically effective amount of Pergolide, a pharmaceutically acceptable salt thereof, or a pharmaceutical composition thereof. In still other embodiments, the method includes administering to a subject in need thereof a therapeutically effective amount of Lisuride, a pharmaceutically acceptable salt thereof, or a pharmaceutical composition thereof. In still other embodiments, the method includes administering to a subject in need thereof a therapeutically effective amount of 2-Bromo-lysergic acid diethylamide (BOL-148), a pharmaceutically acceptable salt thereof, or a pharmaceutical composition thereof. In yet other embodiments, the method includes administering to a subject in need thereof a therapeutically effective amount of Nicergoline, a pharmaceutically acceptable salt thereof, or a pharmaceutical composition thereof. In yet other embodiments, the method includes administering to a subject in need thereof a therapeutically effective amount of Bromocriptine, a pharmaceutically acceptable salt thereof, or a pharmaceutical composition thereof.

In other embodiments, the non-hallucinogenic analog of a psychedelic compound includes Sumatriptan, Zolmitriptan, Rizatriptan, Eletriptan, Naratriptan, Frovatriptan, Almotriptan, 6-methoxy-N,N-dimethyltryptamine, 6-fluoro-N,N-dimethyltryptamine, or combination thereof. In those embodiments, the method includes administering to a subject in need thereof a therapeutically effective amount of the non-hallucinogenic analog of a psychedelic compound including Sumatriptan, Zolmitriptan, Rizatriptan, Eletriptan, Naratriptan, Frovatriptan, Almotriptan, 6-methoxy-N,N-dimethyltryptamine, 6-fluoro-N,N-dimethyltryptamine, combinations thereof, a pharmaceutically acceptable salt thereof, or a pharmaceutical composition thereof.

In some embodiments, the method includes administering to a subject in need thereof a therapeutically effective amount of Sumatriptan, a pharmaceutically acceptable salt thereof, or a pharmaceutical composition thereof. In some embodiments, the method includes administering to a subject in need thereof a therapeutically effective amount of Zolmitriptan, a pharmaceutically acceptable salt thereof, or a pharmaceutical composition thereof. In some embodiments, the method includes administering to a subject in need thereof a therapeutically effective amount of Rizatriptan, a pharmaceutically acceptable salt thereof, or a pharmaceutical composition thereof. In some embodiments, the method includes administering to a subject in need thereof a therapeutically effective amount of Eletriptan, a pharmaceutically acceptable salt thereof, or a pharmaceutical composition thereof. In other embodiments, the method includes administering to a subject in need thereof a therapeutically effective amount of Naratriptan, a pharmaceutically acceptable salt thereof, or a pharmaceutical composition thereof. In other embodiments, the method includes administering to a subject in need thereof a therapeutically effective amount of Frovatriptan, a pharmaceutically acceptable salt thereof, or a pharmaceutical composition thereof. In other embodiments, the method includes administering to a subject in need thereof a therapeutically effective amount of Almotriptan, a pharmaceutically acceptable salt thereof, or a pharmaceutical composition thereof. In still other embodiments, the method includes administering to a subject in need thereof a therapeutically effective amount of 6-methoxy-N,N-dimethyltryptamine, a pharmaceutically acceptable salt thereof, or a pharmaceutical composition thereof. In still other embodiments, the method includes administering to a subject in need thereof a therapeutically effective amount of 6-fluoro-N,N-dimethyltryptamine, a pharmaceutically acceptable salt thereof, or a pharmaceutical composition thereof.

In some embodiments, the method includes administering a second agent (e.g. therapeutic agent). In some embodiments, the method includes administering a second agent (e.g. therapeutic agent) in a therapeutically effective amount. In some embodiments, the second agent is an agent for treating a brain disorder. In some embodiments, the second agent is an anti-psychiatric disorder agent. In other embodiments, the second agent is an anti-substance use disorder agent. In other embodiments, the second agent is an anti-neurodegenerative agent.

In some embodiments, the subject is not already being treated with Ergometrine for postpartum hemorrhage and postabortion hemorrhage due to uterine atony.

In some embodiments, the subject is not already being treated with Dihydroergotamine for migraines or cluster headaches.

In some embodiments, the subject is not already being treated with Methylergometrine for routine management after delivery of the placenta, postpartum atony and hemorrhage, subinvolution, or migraines.

In some embodiments, the subject is not already being treated with Methysergide for migraines or cluster headaches.

In some embodiments, the subject is not already being treated with Ergotamine for migraines or cluster headaches.

In some embodiments, the subject is not already being treated with Cabergoline for hyperprolactinemic disorders or Parkinson's disease.

In some embodiments, the subject is not already being treated with Pergolide for Parkinson's disease.

In some embodiments, the subject is not already being treated with Lisuride for Parkinson's disease.

In some embodiments, the subject is not already being treated with Nicergoline for senile dementia or other disorders with vascular origins.

In some embodiments, the subject is not already being treated with Bromocriptine for pituitary tumors, Parkinson's disease, hyperprolactinaemia, neuroleptic malignant syndrome, or type 2 diabetes.

In other embodiments, the subject is not already being treated with Sumatriptan for migraines or cluster headaches.

In other embodiments, the subject is not already being treated with Zolmitriptan for migraines or cluster headaches.

In other embodiments, the subject is not already being treated with Rizatriptan for migraines or cluster headaches.

In still other embodiments, the subject is not already being treated with Eletriptan for migraines or cluster headaches.

In still other embodiments, the subject is not already being treated with Naratriptan for migraines or cluster headaches.

In yet other embodiments, the subject is not already being treated with Frovatriptan for migraines or cluster headaches.

In yet other embodiments, the subject is not already being treated with Almotriptan for migraines or cluster headaches.

In one specific embodiment, the method for treating the brain disorder includes administering to a subject in need thereof a therapeutically effective amount of Ergometrine, a pharmaceutically acceptable salt thereof, or a pharmaceutical composition thereof, provided the subject is not already being treated with Ergometrine for postpartum hemorrhage and postabortion hemorrhage due to uterine atony.

In one specific embodiment, the method for treating the brain disorder includes administering to a subject in need thereof a therapeutically effective amount of Dihydroergotamine, a pharmaceutically acceptable salt thereof, or a pharmaceutical composition thereof, provided the subject is not already being treated with Dihydroergotamine for migraines or cluster headaches.

In one specific embodiment, the method for treating the brain disorder includes administering to a subject in need thereof a therapeutically effective amount of Methylergometrine, a pharmaceutically acceptable salt thereof, or a pharmaceutical composition thereof, provided the subject is not already being treated with Methylergometrine for routine management after delivery of the placenta, postpartum atony and hemorrhage, subinvolution, or migraines.

In one specific embodiment, the method for treating the brain disorder includes administering to a subject in need thereof a therapeutically effective amount of Methysergide, a pharmaceutically acceptable salt thereof, or a pharmaceutical composition thereof, provided the subject is not already being treated with Methysergide for migraines or cluster headaches.

In one specific embodiment, the method for treating the brain disorder includes administering to a subject in need thereof a therapeutically effective amount of Ergotamine, a pharmaceutically acceptable salt thereof, or a pharmaceutical composition thereof, provided the subject is not already being treated with Ergotamine for migraines or cluster headaches.

In one specific embodiment, the method for treating the brain disorder includes administering to a subject in need thereof a therapeutically effective amount of Cabergoline, a pharmaceutically acceptable salt thereof, or a pharmaceutical composition thereof, provided the subject is not already being treated with Cabergoline for hyperprolactinemic disorders or Parkinson's disease.

In one specific embodiment, the method for treating the brain disorder includes administering to a subject in need thereof a therapeutically effective amount of Pergolide, a pharmaceutically acceptable salt thereof, or a pharmaceutical composition thereof, provided the subject is not already being treated with Pergolide for Parkinson's disease.

In one specific embodiment, the method for treating the brain disorder includes administering to a subject in need thereof a therapeutically effective amount of Lisuride, a pharmaceutically acceptable salt thereof, or a pharmaceutical composition thereof, provided the subject is not already being treated with Lisuride for Parkinson's disease.

In one specific embodiment, the method for treating the brain disorder includes administering to a subject in need thereof a therapeutically effective amount of Nicergoline, a pharmaceutically acceptable salt thereof, or a pharmaceutical composition thereof, provided the subject is not already being treated with Nicergoline for senile dementia or other disorders with vascular origins.

In one specific embodiment, the method for treating the brain disorder includes administering to a subject in need thereof a therapeutically effective amount of Bromocriptine, a pharmaceutically acceptable salt thereof, or a pharmaceutical composition thereof, provided the subject is not already being treated with Bromocriptine for pituitary tumors, Parkinson's disease, hyperprolactinaemia, neuroleptic malignant syndrome, or type 2 diabetes.

In another specific embodiment, the method for treating the brain disorder includes administering to a subject in need thereof a therapeutically effective amount of Sumatriptan, a pharmaceutically acceptable salt thereof, or a pharmaceutical composition thereof, provided the subject is not already being treated with Sumatriptan for migraines or cluster headaches.

In another specific embodiment, the method for treating the brain disorder includes administering to a subject in need thereof a therapeutically effective amount of Zolmitriptan, a pharmaceutically acceptable salt thereof, or a pharmaceutical composition thereof, provided the subject is not already being treated with Zolmitriptan for migraines or cluster headaches.

In another specific embodiment, the method for treating the brain disorder includes administering to a subject in need thereof a therapeutically effective amount of Rizatriptan, a pharmaceutically acceptable salt thereof, or a pharmaceutical composition thereof, provided the subject is not already being treated with Rizatriptan for migraines or cluster headaches.

In still another specific embodiment, the method for treating the brain disorder includes administering to a subject in need thereof a therapeutically effective amount of Eletriptan, a pharmaceutically acceptable salt thereof, or a pharmaceutical composition thereof, provided the subject is not already being treated with Eletriptan for migraines or cluster headaches.

In still another specific embodiment, the method for treating the brain disorder includes administering to a subject in need thereof a therapeutically effective amount of Naratriptan, a pharmaceutically acceptable salt thereof, or a pharmaceutical composition thereof, provided the subject is not already being treated with Naratriptan for migraines or cluster headaches.

In yet another specific embodiment, the method for treating the brain disorder includes administering to a subject in need thereof a therapeutically effective amount of Frovatriptan, a pharmaceutically acceptable salt thereof, or a pharmaceutical composition thereof, provided the subject is not already being treated with Frovatriptan for migraines or cluster headaches.

In yet another specific embodiment, the method for treating the brain disorder includes administering to a subject in need thereof a therapeutically effective amount of Almotriptan, a pharmaceutically acceptable salt thereof, or a pharmaceutical composition thereof, provided the subject is not already being treated with Almotriptan for migraines or cluster headaches.

VIII. Examples

Example 1: Chemicals and Reagents

Chemicals were purchased from commercial sources such as Rizatriptan benzoate salt (RZT, Sigma-Aldrich), Lisuride (LIS, Tocris), bromocriptine mesylate (BCP, Tocris), cabergoline (CAB, Tocris), ANA-12 (MedChem Express), rapamycin (RAPA, Alfa Aesar), ketanserin (KETSN, ApexBio), and brain-derived neurotrophic factor (BDNF, Sigma-Aldrich).

Several compounds including 6-methoxy-N,N-dimethyltryptamine (6MT) and 6-fluoro-N,N-dimethyltryptamine (6FT) were synthesized via the following procedures, and judged to be analytically pure based on NMR and LC-MS data.

Example 1.1: Synthesis of
6-fluoro-N,N-dimethyltryptamine (6FT)

To an ice-cold solution of 6-fluoroindole (300 mg, 2.22 mmol) in diethyl ether (7.5 mL) was added oxalyl chloride (0.191 ml, 2.22 mmol, 1 equiv). The reaction was warmed to room temperature and stirred for 30 min. The resulting precipitate was filtered and washed with several portions of ice-cold ether. This material was suspended in ether (14 ml) and cooled to 0° C. followed by dropwise addition of 2M dimethylamine (2.44 ml, 4.88 mmol, 2.2 equiv). The reaction was warmed to room temperature and stirred for 1 h at which point a precipitate had formed. The precipitate was filtered, washed with ice-cold ether, and dried to yield a white solid (271 mg, 52%). The unpurified material was dissolved in 2 ml of THF and cooled to 0° C. To this solution was added lithium aluminum hydride (236 mg, 6.21 mmol, 12 equiv) in ether (5 ml). The reaction was heated at reflux for 12 h, cooled to 0° C., and quenched using isopropyl alcohol until gas evolution subsided. The unpurified mixture was added to a saturated solution of Rochelle's salt (100 mL) and extracted 3 times with $CH_2Cl_2$ (25 mL). The organic phases were combined, dried over $Na_2SO_4$, filtered, and concentrated under reduced pressure. The unpurified material was dissolved in acetone (10 ml) and added to a boiling solution of fumaric acid (28.5 mg, 0.246 mmol, 0.5 equiv) in acetone (20 mL). A precipitate formed immediately and the solution was allowed to cool to room temperature, filtered, and washed with cold acetone to yield a white solid. The resulting solid was dried under reduced pressure to yield pure compound as the fumarate salt (2:1 6-FT: fumaric acid, 52 mg, 13% over 3 steps). TLC (6-FT free base) $R_f$=0.22 (9:1 $CH_2Cl_2$:MeOH 1% $NH_4OH_{(aq)}$). $^1H$ NMR (600 MHz, DMSO-$d_6$) δ 10.91 (s, 1H), 7.52 (dd, 1H, J=5.5, 3.1, Hz), 7.16 (s, 1H), 7.10 (dd, 1H, J=7.8, 2.3 Hz), 6.84 (td, 1H, J=7.4, 2.35, Hz), 6.54 (s, 1H), 2.88 (t, 2H, J=8.3, Hz), 2.75 (t, 2H, J=8.5, Hz), 2.40 (s, 6H). $^{13}C$ NMR (100 MHz, DMSO-$d_6$) 167.7, 159.6, 158.1, 136.0, 134.9, 123.7, 119.3, 111.0, 106.8, 97.4, 57.8, 43.1, 21.1 ppm IR (diamond, ATR) v 3330, 3066, 2401, 1691, 1627, 1562 $cm^{-1}$.

Example 1.2: Synthesis of 6-methoxy-N,N-dimethyltryptamine (6MT)

To an ice-cold solution of 6-methoxyindole (189 mg, 1.28 mmol) in 4.5 ml of diethyl ether was added oxalyl chloride (0.110 ml, 1.28 mmol, 1 equiv). The reaction was warmed to room temperature and stirred for 30 min. The resulting precipitate was filtered and washed with several portions of ice-cold ether. This material was suspended in ether (14 mL) and cooled to 0° C. followed by dropwise addition of 2M dimethylamine (1.4 ml, 2.83 mmol, 2.2 equiv). The reaction was warmed to room temperature and stirred for 1 h at which point a precipitate had formed. The precipitate was filtered, washed with ice-cold ether, and dried to yield a tan solid (140 mg, 44%). The unpurified material (105 mg, 0.427 mmol, 1 equiv) was taken up in 2 ml of THF and cooled to 0° C. To this solution was added 4M lithium aluminum hydride in ether (0.5 ml, 2.1 mmol, 5 equiv). The reaction was heated at reflux for 12 h. The reaction was then cooled to 0° C. and quenched using isopropyl alcohol until gas evolution subsided. A saturated solution of Rochelle's salt (100 mL) was added and extracted 3 times with $CH_2Cl_2$ (25 mL). The unpurified oil was dissolved in acetone (10 mL) and added to a boiling solution of fumaric acid (25 mg, 0.213 mmol, 0.5 equiv) in acetone (10 mL). A precipitate formed immediately and the solution was allowed to cool to room temperature, filtered, and washed with cold acetone to yield a tan solid. The resulting solid was dried under reduced pressure to yield pure compound as the fumarate salt (2:1 6-MT:fumaric acid, 55 mg, 21% over 3 steps). TLC (6-MT free base) $R_f$=0.22 (9:1 $CH_2Cl_2$:MeOH 1% $NH_4OH_{(aq)}$). $^1H$ NMR (600 MHz, DMSO-$d_6$) δ 10.64 (s, 1H), 7.39 (d, 1H J=8.6 Hz), 7.01 (s, 1H), 6.83 (d, 1H, J=2.2 Hz), 6.63 (dd, 1H, J=6.3, 2.3 Hz), 6.50 (s, 1H), 3.74 (s, 3H), 2.86 (t, 2H, J=8.7, Hz), 2.77 (t, 2H, J=8.7 Hz), 2.42 (s, 6H). $^{13}C$ NMR (100 MHz, DMSO-$d_6$) 168.2, 155.5, 136.9, 135.1, 121.4, 121.3, 118.9, 111.1, 108.5, 94.4, 58.4, 55.1, 43.6, 21.8 ppm. IR (diamond, ATR) v 3112, 3081, 2918, 2837, 1629, 1558 $cm^1$.

Example 2: General In Vitro and In Vivo Methods

Example 2.1: Animals

Sprague-Dawley rats were obtained from Charles River Laboratories (Wilmington, MA, USA). All experimental procedures involving animals were approved by the University of California, Davis Institutional Animal Care and Use Committee (IACUC) and adhered to principles described in the National Institutes of Health Guide for the Care and Use of Laboratory Animals. The University of California, Davis is accredited by the Association for Assessment and Accreditation of Laboratory Animal Care, International (AAALAC), and has an Animal Welfare Assurance number (#A3433-01) on file with the Office of Laboratory Animal Welfare (OLAW).

Example 2.2: Cell Culture

Primary cortical cultures were prepared using tissue from embryonic day 18 (E18) Sprague Dawley rats. Cells were plated at various densities on poly-D-lysine coated plates depending on the specific experiment (vide infra). Plating media consisted of 10% heat-inactivated FBS (Life Technologies), 1% penicillin-streptomycin (Life Technologies), and 0.5 mM glutamine (Life Technologies) in Neurobasal (Life Technologies). After 15-24 h, the media was removed and exchanged for replacement media containing 1×B27 supplement (Life Technologies), 1% penicillin-streptomycin, 0.5 mM glutamine, 12.5 µM glutamate, and Neurobasal. After 96 h, 50% of the media was removed and replaced with feed media containing 1×B27 supplement, 1% penicillin-streptomycin, and 0.5 mM glutamine. Once per week until the cultures had reached sufficient maturity for experiments, 50% of the culture media was removed and replaced with feed media, with an additional 20% by volume being added to account for evaporation. For experiments using antagonists/inhibitors, cells were pretreated with ANA-12 (10 µM), rapamycin (100 nM), and ketanserin (100 µM) for 10 min prior to the addition of test compounds. The final DMSO concentration of these experiments was 0.2%. The neurons used in each cellular experiment were taken from at least two different treatment wells and the wells were randomized to account for plate effects. All of the cellular experiments were replicated on at least two occasions by two or more experimenters.

Example 2.3: Sample Preparation for In Vitro and In Vivo Studies

All compounds were dissolved in DMSO and diluted 1:1000 with the exception that BDNF was dissolved in water. Cells were treated with the compound at a final concentration of 90 µM (0.1% DMSO) while all other compounds were treated at 10 µM (0.1% DMSO) unless noted otherwise. For in vivo studies, the compound was dissolved in sterile 0.9% saline and administered intraperitoneally at a dose of 10 mg/kg and an injection volume of 10 mL/kg.

Example 2.4: Neuritogenesis Experiments

After 3 days in vitro (DIV 3), approximately 50,000 cells/well in poly-D-lysine coated 24 well plates were treated. Treatment was accomplished by first diluting DMSO stock solutions of compounds 1:10 in Neurobasal followed by a 1:100 dilution into each well (total dilution=1: 1000). After 72 h, cells were fixed by removing 80% of the media and replacing it with a volume of 4% aqueous paraformaldehyde (Alfa Aesar) equal to 50% of the working volume of the well. Then, the cells were allowed to sit for 20 min at room temperature before the fixative was aspirated and each well washed twice with DPBS. Cells were permeabilized using 0.2% Triton X-100 (ThermoFisher) in DPBS for 20 minutes at room temperature without shaking. Plates were blocked with antibody diluting buffer (ADB) containing 2% bovine serum albumin (BSA) in DPBS for 1 h at room temperature. Then, plates were incubated overnight at 4° C. with gentle shaking in ADB and a chicken anti-MAP2 antibody (1:10,000; EnCor, CPCA-MAP2). The next day, plates were washed three times with DPBS and once with 2% ADB in DPBS. Plates were incubated for 1 h at room temperature in ADB containing an anti-chicken IgG secondary antibody conjugated to Alexa Fluor 488 (Life Technologies, 1:500) and washed five times with DPBS. After the final wash, 500 µL of DPBS was added per well and imaged on a Leica inverted epifluorescence microscope at 40× magnification. Images were analyzed using the Simple Neurite Tracer and Sholl analysis plug-ins for ImageJ Fiji (version 1.51N). All images were taken and analyzed by an experimenter blinded to treatment conditions.

Example 2.5: *Drosophila* Experiments

For fly stocks, the Gal4 driver line, 221-Gal4, was used to drive the expression of the membrane marker, UAS-cd4-tdGFP, to visualize dendrite morphology for all conditions. For morphological analysis, 221-Gal14 with UAS-cd4-tdGFP were crossed and the progeny at either the first larval instar (early treatment) or late second larval instar (late treatment) was collected, then the larvae were transferred to grape agar plates smeared with yeast paste. This yeast paste was dissolved in 1 mL of autoclaved water containing 0.1% DMSO with or without compounds dissolved at concentration of 10 µM. Whole, live wandering third instar larvae were mounted in 90% glycerol under coverslips sealed with grease and imaged using an Olympus FV1000 laser scanning confocal microscope. Collected Z-stacks containing the dendritic arbors of the class I da sensory neurons were used for analysis. One neuron from segment A3 or A4 was imaged per larvae and three larvae were imaged per drug condition per treatment window (early vs. late treatment). All larval drug treatments were performed at least three separate times. Total dendrite length and the number of branch points were determined from maximum Z projections of the Z-stack image files using the Simple Neurite Tracer plugin for ImageJ Fiji Data acquisition and analysis was performed by an experimenter blinded to treatment conditions.

Example 2.6: Zebrafish Experiments

Wildtype fish (NHGRI-1) were dechorionated 24 h post fertilization (hpf) and placed individually into a 96-well plate containing chemicals of interest (10 µM compound, 0.1% DMSO). Larvae were raised in a light-cycled incubator (28° C.) and subsequently subjected to an activity assay for 16 hours, from 5 pm to 9 am, at 5.5-6.5 days post fertilization (dpf). Specifically, they were imaged using DanioVision with a light cycle mimicking their natural day/night cycle. Subsequently, fish larvae (6.5 dpf) were immediately fixed following the movement assay using 4% aqueous paraformaldehyde overnight. Head-width measurements were performed by imaging larvae dorsally using a stereomicroscope (12× magnifications) and a digital ruler (ImageJ) to measure the distance between the inner edges of each eye. Data acquisition and analysis was performed by an experimenter blinded to treatment conditions.

Example 2.7: Spinogenesis Experiments

Cells were plated at a density of 35,000 cells/well on glass coverslips in 24 well plates. At DIV 18, cells were treated for 24 h and fixed as described for the neuritogenesis experiments (vide supra). Fixative was aspirated and each well washed twice with DPBS. Cells were permeabilized using 0.2% Triton X-100 (ThermoFisher) in DPBS for 20 minutes at room temperature without shaking. Plates were blocked with antibody diluting buffer (ADB) containing 2% bovine serum albumin (BSA) in DPBS for 1 h at room temperature. Then, plates were incubated overnight at 4° C. with gentle shaking in ADB and anti-chicken MAP2 (1:10,000; EnCor, CPCA-MAP2). The next day, plates were washed three times with DPBS and once with 2% ADB in DPBS. Plates were incubated for 1 h at room temperature in ADB containing an anti-chicken IgG secondary antibody conjugated to Alexa Fluor 568 (Life Technologies, 1:500) and phalloidin conjugated to Alexa Fluor 488 (Life Technologies, 1:40). Then, the cells were washed five times with DPBS. Finally, the coverslips were mounted onto microscope slides using ProLong Gold (Life Technologies) and allowed to cure for 24 hours at room temperature. Images of secondary dendrites were taken using a Nikon N-SIM Structured Illumination Super-resolution Microscope with a 100×/NA 1.49 objective, 100 EX V-R diffraction grating, and an Andor iXon3 DU-897E EMCCD. Images were recollected and reconstructed in the "2D-SIM" mode (no out of focus light removal; reconstruction used three diffraction grating angles each with three translations). Dendritic spines were counted manually by a trained experimenter who was blinded to the treatment conditions.

Example 2.8: Synaptogenesis Experiments

Cells were plated at a density of 35,000 cells/well on glass coverslips in 24 well plates. At DIV 18, cells were treated for 24 h and fixed as described for the neuritogenesis experiments (vide supra). Fixative was aspirated and each well washed twice with DPBS. Cells were permeabilized using 0.2% Triton X-100 (ThermoFisher) in DPBS for 20 minutes at room temperature without shaking. Plates were blocked with antibody diluting buffer (ADB) containing 2% bovine serum albumin (BSA) in DPBS for 1 h at room temperature. Then, plates were incubated overnight at 4° C. with gentle shaking in ADB and anti-MAP2 (1:10,000; EnCor, CPCA-MAP2), anti-VGLUT1 (Millipore, AB5905, 1:1000), and anti-PSD-95 (Millipore, MABN68, 1:500) antibodies. The next day, plates were washed three times with DPBS and once with 2% ADB in DPBS. Plates were incubated for 1 h at room temperature in ADB containing secondary antibodies conjugated to Alexa Fluor 488 (Life Technologies, 1:500), Cy3 (Jackson ImmunoResearch Inc, 1:500), or Alexa Fluor 647 (Jackson ImmunoResearch Inc, 1:500). Images of secondary dendrites were collected using a confocal microscope (Olympus FV1000) with a 60× oil objective and a 1.42 numerical aperture.

Synaptic density and size as well as PSD-95 and VGLUT1 densities were determined using custom software that works in three stages. The first stage was a foreground/background separation that outputs a mask of pixels within the image that corresponded to the neuron. Next, puncta of synaptic proteins were identified using only pixels belonging to the foreground mask from the first stage. Finally, synapses were identified as colocalizations of puncta of pre- and post-synaptic proteins. The foreground mask was determined using a fluorescence intensity threshold chosen to maximize the connectedness of both the foreground and the background. Specifically, for a given threshold, connected pixels that passed the threshold were clustered together, and connected pixels that fell below threshold were clustered together. The average cluster size was computed for each type of cluster, and the threshold that maximized the product of these averages was chosen. The resulting foreground mask was cleaned by removing clusters smaller than 0.06

μm² and smoothed by eliminating pixels connected to fewer than three other pixels that passed the threshold and adding pixels connected to more than four pixels that passed the threshold. Within the foreground mask, every pixel that had greater intensity than its neighbors was treated as a seed point for a potential punctum. The median and standard deviation of pixel intensities was computed for foreground pixels in the neighborhood of each seed point. The size of the local neighborhood was made dynamic in order to maintain sufficient statistics, with a minimum size of 5 μm². Seed points with intensities less than 3 standard deviations above the local median were rejected. For seed points that passed this threshold, adjacent pixels that passed a less stringent threshold (the minimum of 2 standard deviations above the median and the average of the median and seed point intensities) were clustered. In order to prevent neighboring puncta from being clustered together, intensities for newly added pixels were required to decrease if adjacent established pixels were already close to the lower threshold. Once the clustering was complete, puncta were smoothed in the same manner as the foreground and rejected if they were smaller than 0.03 μm². Pixels that were part of a punctum passing all of the above criteria were removed from the foreground mask so as not to be included in the threshold calculation for future puncta. After every seed point was tested, those that failed were iterated over again until no new puncta were added. At the beginning of each iteration, puncta that were smaller than the 3 times of the minimum size threshold were removed to be reclustered. Synapses were defined as a colocalization of PSD-95 and VGLUT1 puncta. Two puncta were considered colocalized if they had at least 1 pixel of overlap. Synapse densities as well as the densities of presynaptic and postsynaptic markers were calculated using dendrite areas computed by counting pixels within a region of interest belonging to the foreground mask in the MAP2 channel. Synapse size was calculated using the number of pixels representing each colocalization event. Outliers were removed using the ROUT method in GraphPad Prism (version 7.0a) with a Q value equal to 5%.

Example 2.9: BDNF ELISA Assay

Cortical cultures were grown in 6-well plates (600,000 cells per well). At DIV 17-18, all media was removed and replaced with fresh Neurobasal. After 4 h, each well was treated with compound dissolved in DMSO (1:1000) for 24 h. After the treatment period, the media was removed and the cells washed once with ice-cold DPBS. To each well was added 200 μL of Cell Extraction Buffer (Life Technologies) supplemented with cOmplete and PhoSTOP inhibitors, and incubated on ice for 5-10 min. Plates were scrapped and the contents collected. The samples were centrifuged at 10,000×g for 10 min at 4° C. and subjected to a BDNF ELISA assay (ThermoFisher) as per the manufacturer's protocol with the exception that the colorimetric signal was only allowed to develop for 8 minutes.

Example 2.10: ddPCR

Cortical cultures were grown in 6-well plates (600,000 cells per well) until DIV 17-18. At that time, cells were treated with compounds (1:1000 dilution from DMSO stock solutions) from 24 h. Cells were then lysed using QIAzol Lysis Reagent (QIAGEN) and RNA extracted using the RNeasy isolation kit (QIAGEN) following instructions of the manufacturer. The resulting RNA was converted to cDNA using the iScript cDNA Synthesis Kit (BioRad). Droplets containing PCR master mix and taqman probes for BDNF (ThermoFisher) and ESD (ThermoFisher) were generated using the QX200 Droplet Digital PCR System (BioRad). Following PCR amplification, BDNF signal was quantified and normalized to the housekeeping gene ESD.

Example 2.11: Golgi-Cox Staining

Female Sprague Dawley rats (~8 weeks old) were given an intraperitoneal injection of the compound or vehicle and sacrificed via decapitation 24 h later. Tissue was prepared following the protocol outlined in the FD Neurotechnologies Rapid GolgiStain Kit (FD Neurotechnologies) with slight modifications. Brains were stored in solution C for 2 months prior to slicing into 120 μm sections using a vibratome. These slices were placed onto microscope slides that were pre-coated with (3-aminopropyl)triethoxysilane. Slices were air dried for a week before staining. Slides were immersed in water twice for 2 minutes, DE solution for 10 minutes, and then water for 2 minutes. After this, slides were immersed sequentially in 25% ethanol for 1 minute, 50% ethanol for 4 minutes, 75% ethanol for 4 minutes, 95% ethanol for 4 minutes, and 100% ethanol for 4 minutes. Slides were then briefly dipped into xylenes before being mounted using DPX Mountant For Histology (Sigma), air-dried, and imaged on a Zeiss AxioScope. Spines were traced using Neurolucida software (version 10) at 100× magnification. Data acquisition and analysis was performed by an experimenter blinded to treatment conditions. Data represents individual neurons taken from 3 different animals per treatment.

Example 2.12: Electrophysiology

Female Sprague Dawley rats (~8 weeks old) were given an intraperitoneal injection of the compound or vehicle. After 24 h, rats were transcardially perfused with ice-cold artificial cerebrospinal fluid (ACSF), containing 119 mM NaCl, 26.2 mM NaHCO$_3$, 11 mM glucose, 2.5 mM KCl, 1 mM NaH$_2$PO$_4$, 2.5 mM CaCl$_2$ and 1.3 mM MgSO$_4$. Brains were rapidly removed and 300 m coronal slices from the mPFC were cut on a Leica VT1200 vibratome (Buffalo Grove, IL) with ice-cold NMDG solution, containing 93 mM NMDG, 93 mM HCl, 2.5 mM KCl, 1.2 mM NaH$_2$PO$_4$, 30 mM NaHCO$_3$, 20 mM HEPES, 25 mM glucose, 5 mM sodium ascorbate, 2 mM thiourea, 3 mM sodium pyruvate, 10 mM MgSO$_4$, and 0.5 mM CaCl$_2$. Slices were incubated in 32° C. NMDG solution for 10 minutes, transferred to room temperature ACSF, and held for at least 50 minutes before recording. All solutions were vigorously perfused with 95% 02 and 5% CO$_2$. Spontaneous excitatory postsynaptic currents (sEPSCs) were recorded at −70 mV in 32° C. ACSF. Cells were patched with 3-5 MS borosilicate pipettes filled with intracellular solution containing 135 mM cesium methanesulfonate, 8 mM NaCl, 10 mM HEPES, 0.3 mM Na-GTP, 4 mM Mg-ATP, 0.3 mM EGTA, and 5 mM QX-314 (Sigma, St Louis, MO). Series resistance was monitored throughout experiments; cells were discarded if series resistance varied more than 25%. All recordings were obtained with a Multiclamp 700B amplifier (Molecular Devices, Sunnyvale, CA). Analysis was performed with the Mini Analysis program (Synaptosoft, Decatur, GA) with a 4 pA detection threshold. Data represented individual neurons taken from 3 different animals per treatment. For statistical comparisons of cumulative distributions, the non-parametric Kolmogorov-Smirnov (KS) test was used. Data acquisition and analysis was performed by experimenters blinded to treatment conditions.

Example 2.13: Statistical Analysis

Statistical analyses were performed using GraphPad Prism (version 7.0a). For analyses involving comparison of three or more groups, a one-way analysis of variance (Dunnett's post-hoc test) was utilized. For the in vivo spine experiment comparing the compound to vehicle treatment, a student's t-test was used. No statistics were calculated for the individual points of the Sholl plots. Instead, statistical analyses were performed on the aggregate data (i.e., the area under the curve of the Sholl plot). Probability distributions from electrophysiology experiments were compared using a Kolmogorov-Smirnov test. The p values of statistical analysis are represented as *$P<0.05$, $P<0.01$, *$P<0.001$, ****$P<0.0001$, as compared to vehicle control.

Example 3: In Vitro Studies of Neuritogenesis and Spinogenesis

Figure 1E:
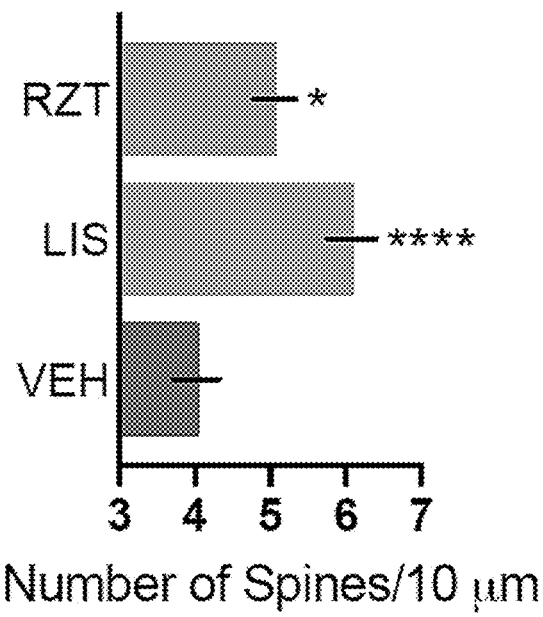
FIG. 1E shows quantification of spine density of cultured embryonic rat cortical neurons (19 days in vitro) treated with compounds for 24 h (n=18-20 neurons, 18 days in vitro).
Figure 2A:
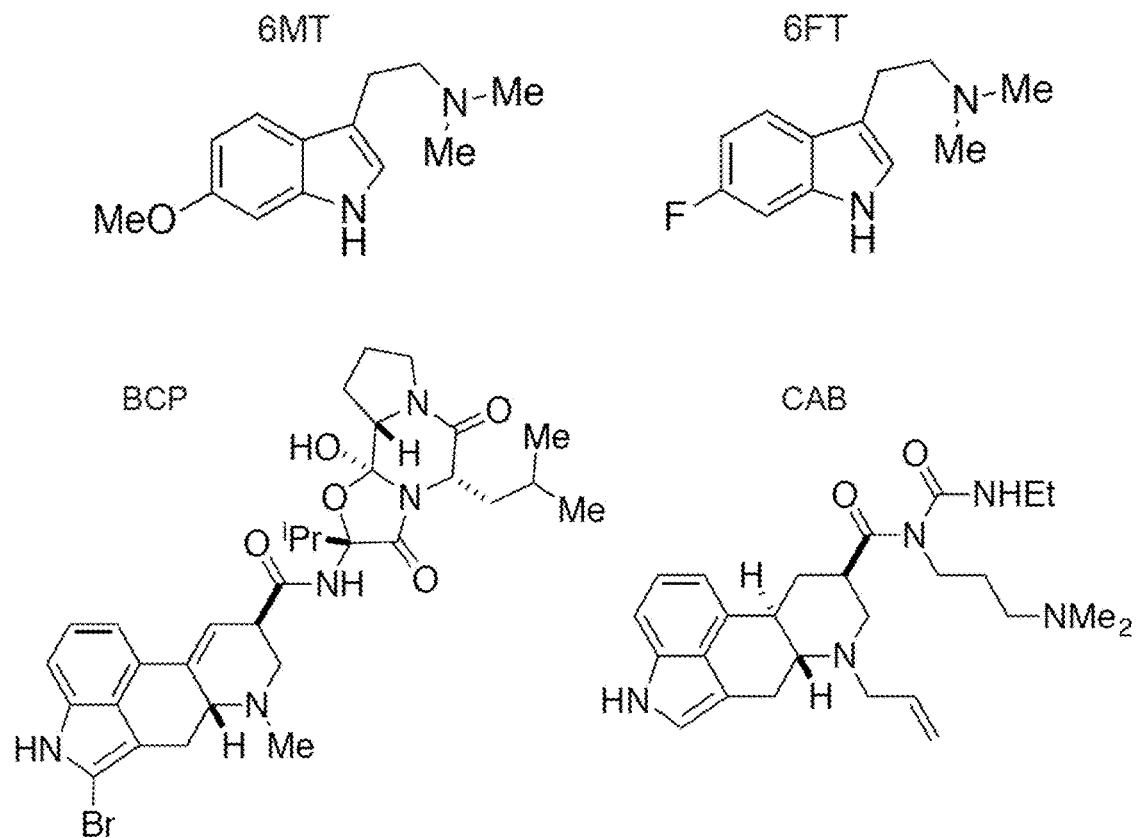
FIG. 2A shows chemical structures of 6-methoxy-N,N-dimethyltryptamine (6MT), 6-Fluoro-N,N-dimethyltryptamine (6FT), Bromocriptine (BCP), and Cabergoline (CAB).
Figure 2B:
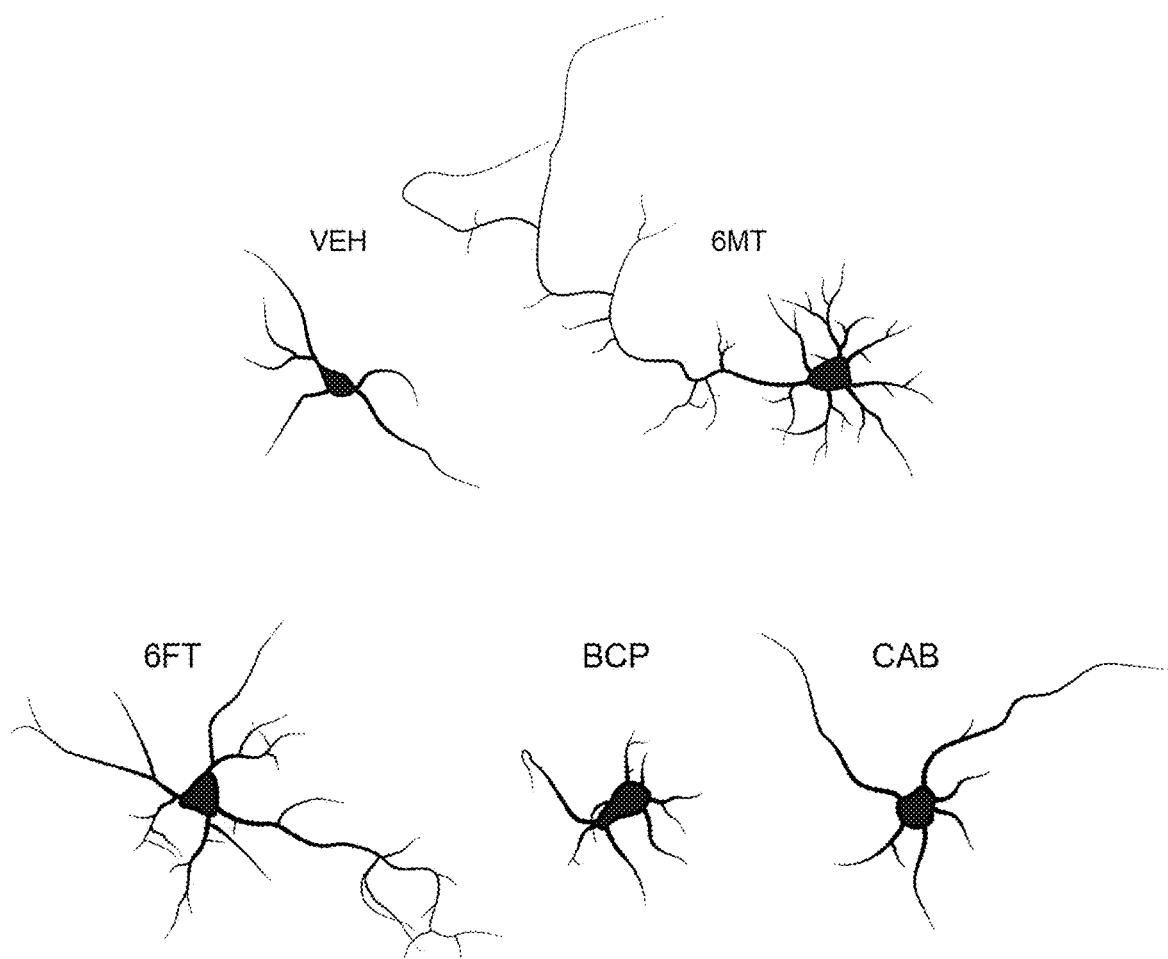
FIG. 2B shows representative tracings of cultured embryonic rat cortical neurons (6 days in vitro) treated with compounds.
Figure 2C:
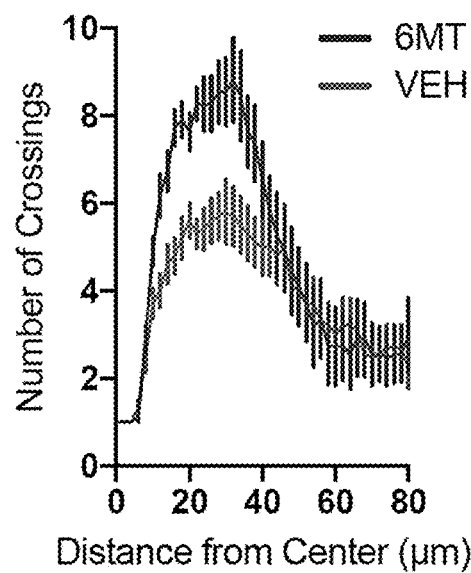
FIG. 2C shows Sholl plots by Sholl analysis (circle radii=2 μm increments) (n=9-11 neurons per treatment).
Figure 2C:
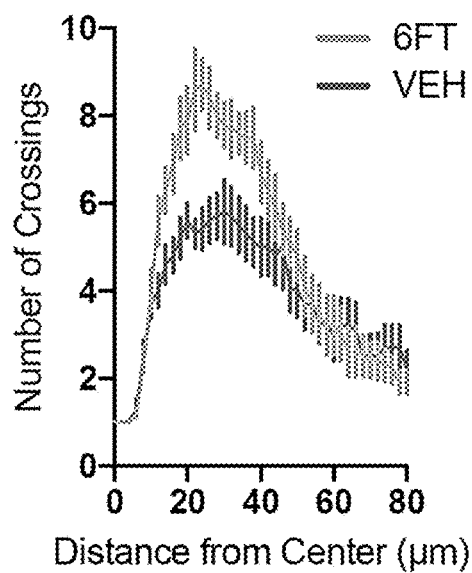
Figure 2C:
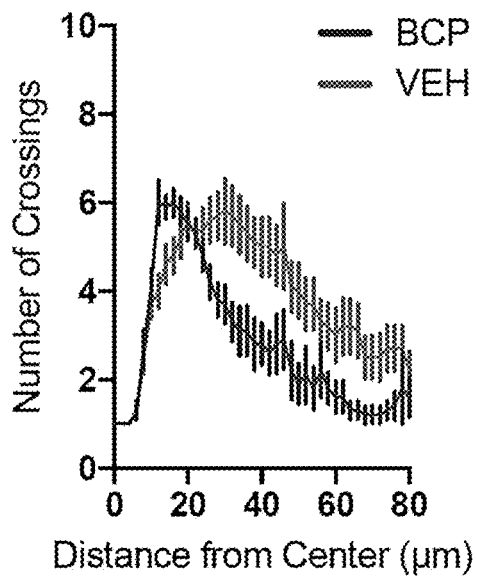
Figure 2C:
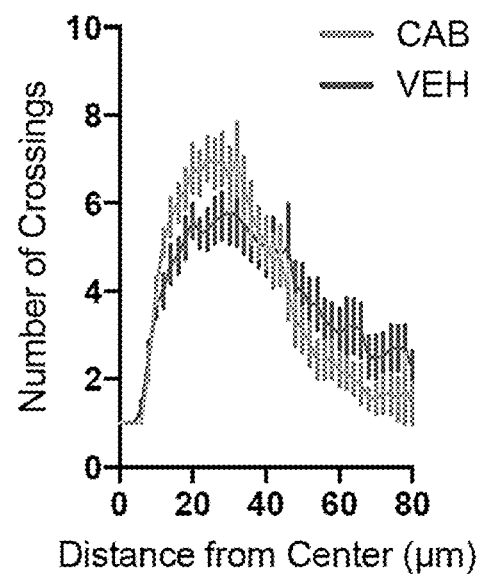
Figure 2D:
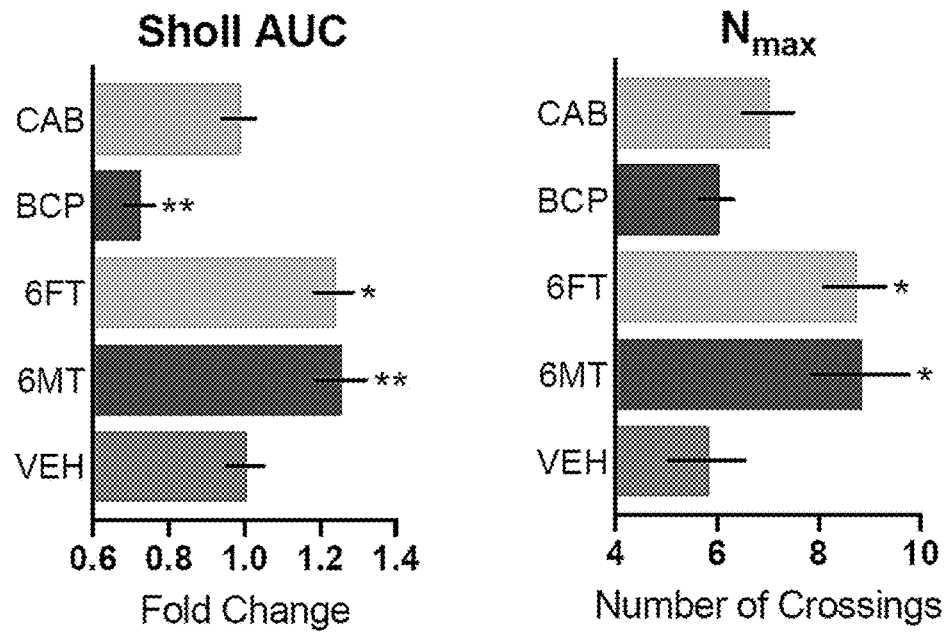
FIG. 2D shows area under the curve (AUC), maximum number of crossings ($N_{max}$), and number of branches determined from the Sholl plots, respectively.
Figure 2D:
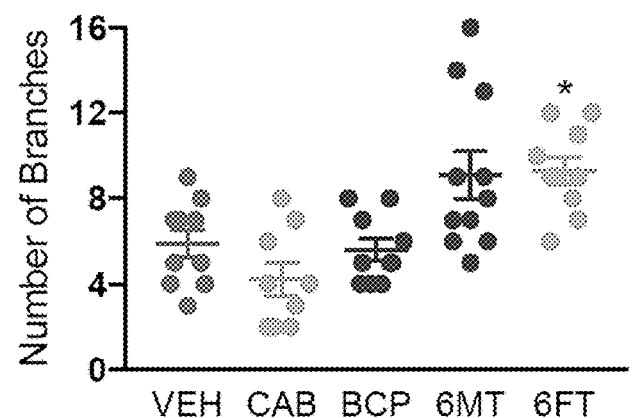
Figure 2E:
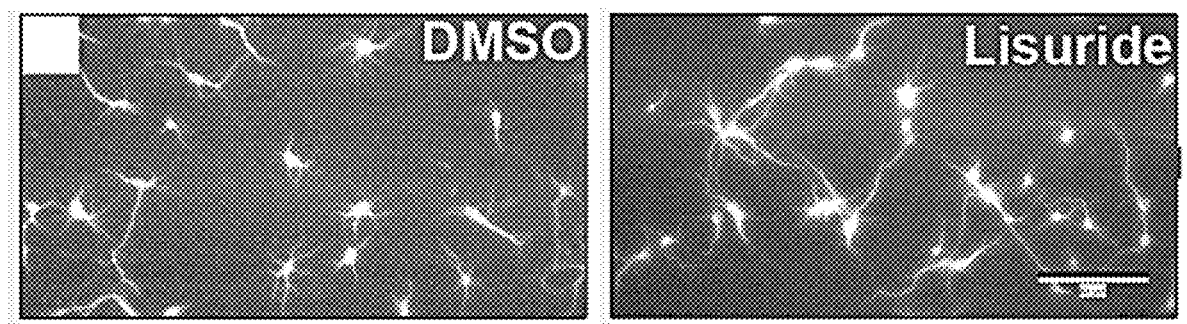
FIG. 2E shows images of increased structural plasticity of neurons after treatment with Lisuride vs. the vehicle (DMSO).

The non-hallucinogenic analogs of tryptamine and ergoline psychedelics (FIG. 1A and FIG. 2A) were tested in both neuritogenesis and spinogenesis assays. Several of these non-hallucinogenic analogs (lisuride, rizatriptan, 6-methoxy-DMT, and 6-fluoro-DMT) were capable of robustly promoting neuritogenesis (see FIGS. 1B to 1D and FIGS. 2B to 2D) while others (bromocriptine and cabergoline) could not. Moreover, lisuride and rizatriptan, non-hallucinogenic structural analogs of LSD and DMT, respectively, both increased spinogenesis in cortical cultures (see FIG. 1E and FIG. 2E).

Figure 3A:
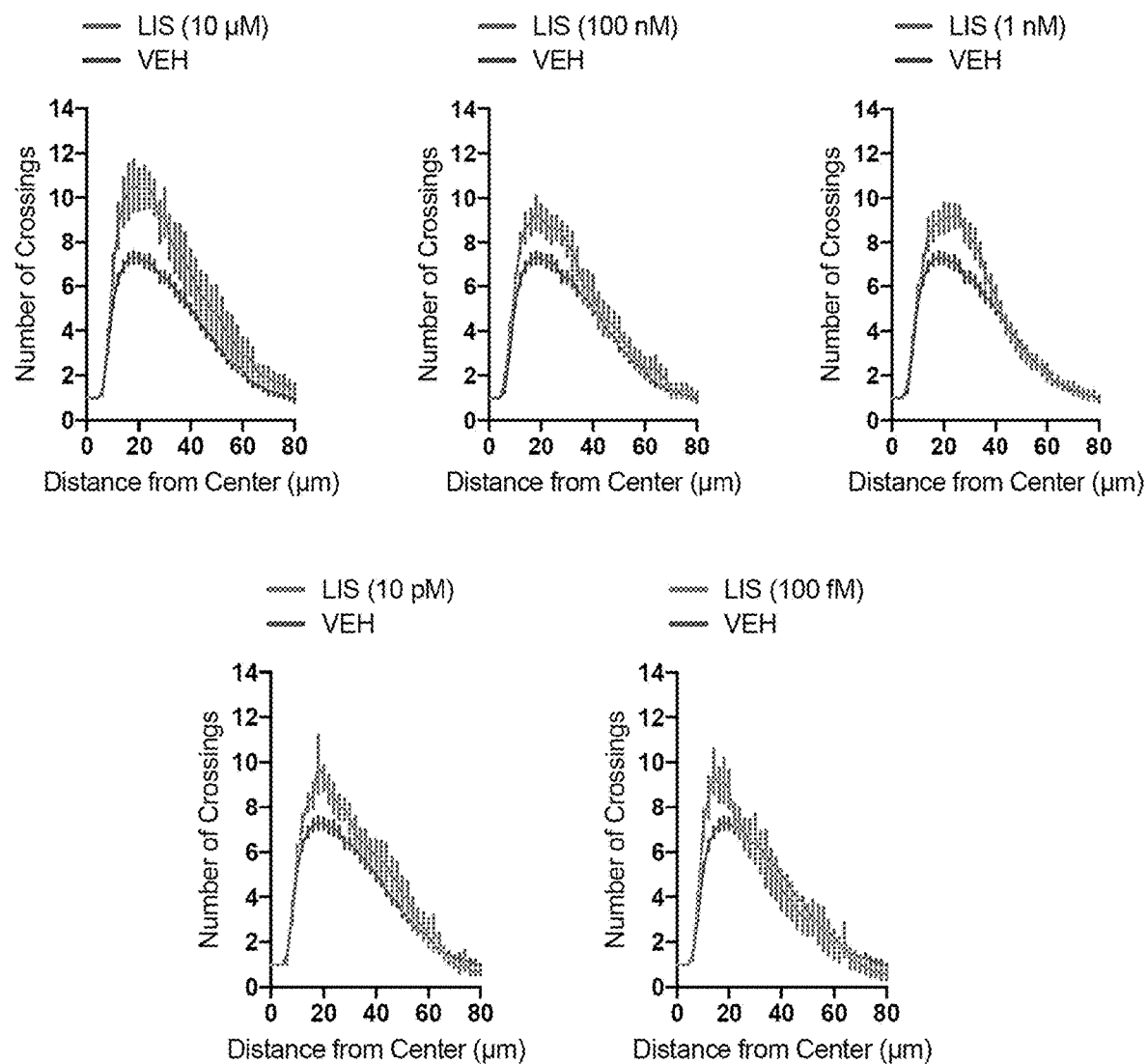
FIG. 3A shows dose responses of Sholl plots comparing Lysergic acid diethylamide (LSD) to Lisuride.
Figure 3B:
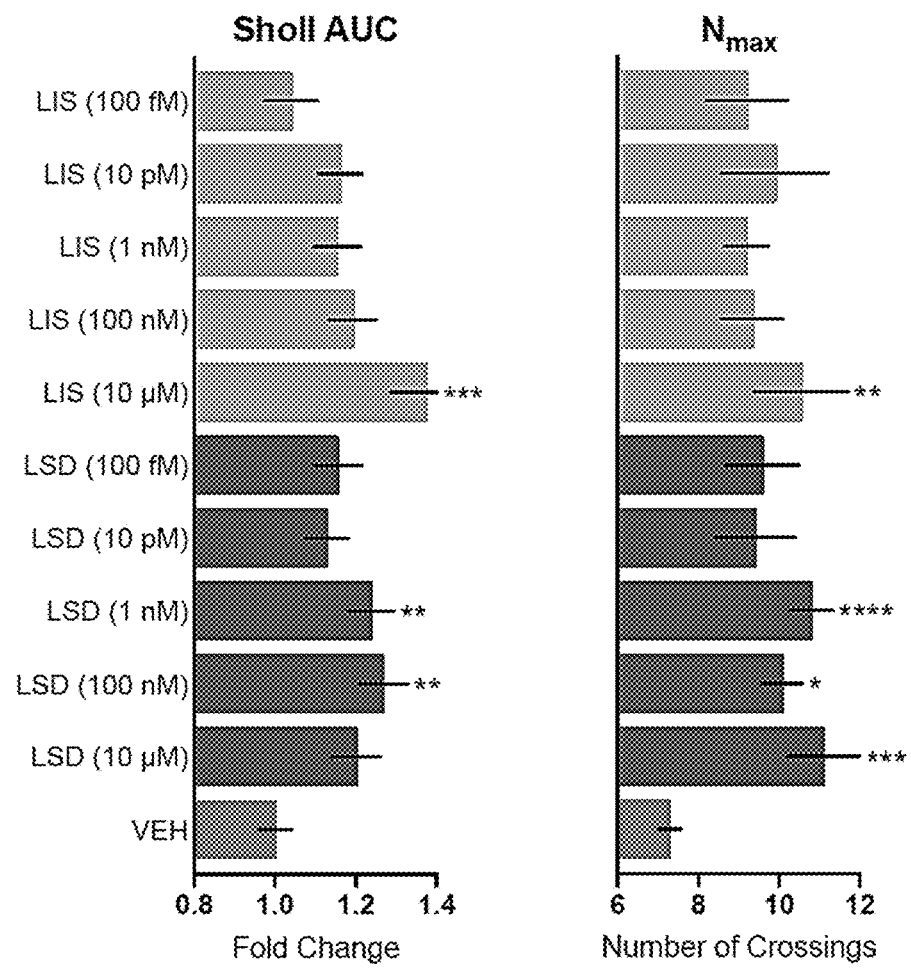
FIG. 3B shows dose responses of LSD and Lisuride on neuritogenesis including area under the curve (AUC), maximum number of crossings ($N_{max}$), and number of branches determined from the Sholl plots, respectively.
Figure 3B:
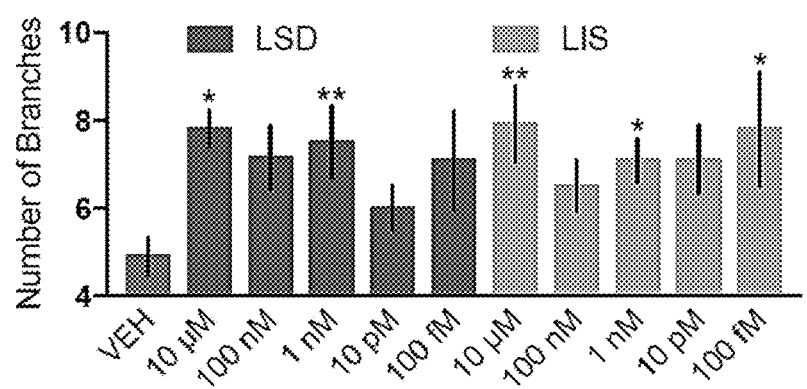
Figure 4:
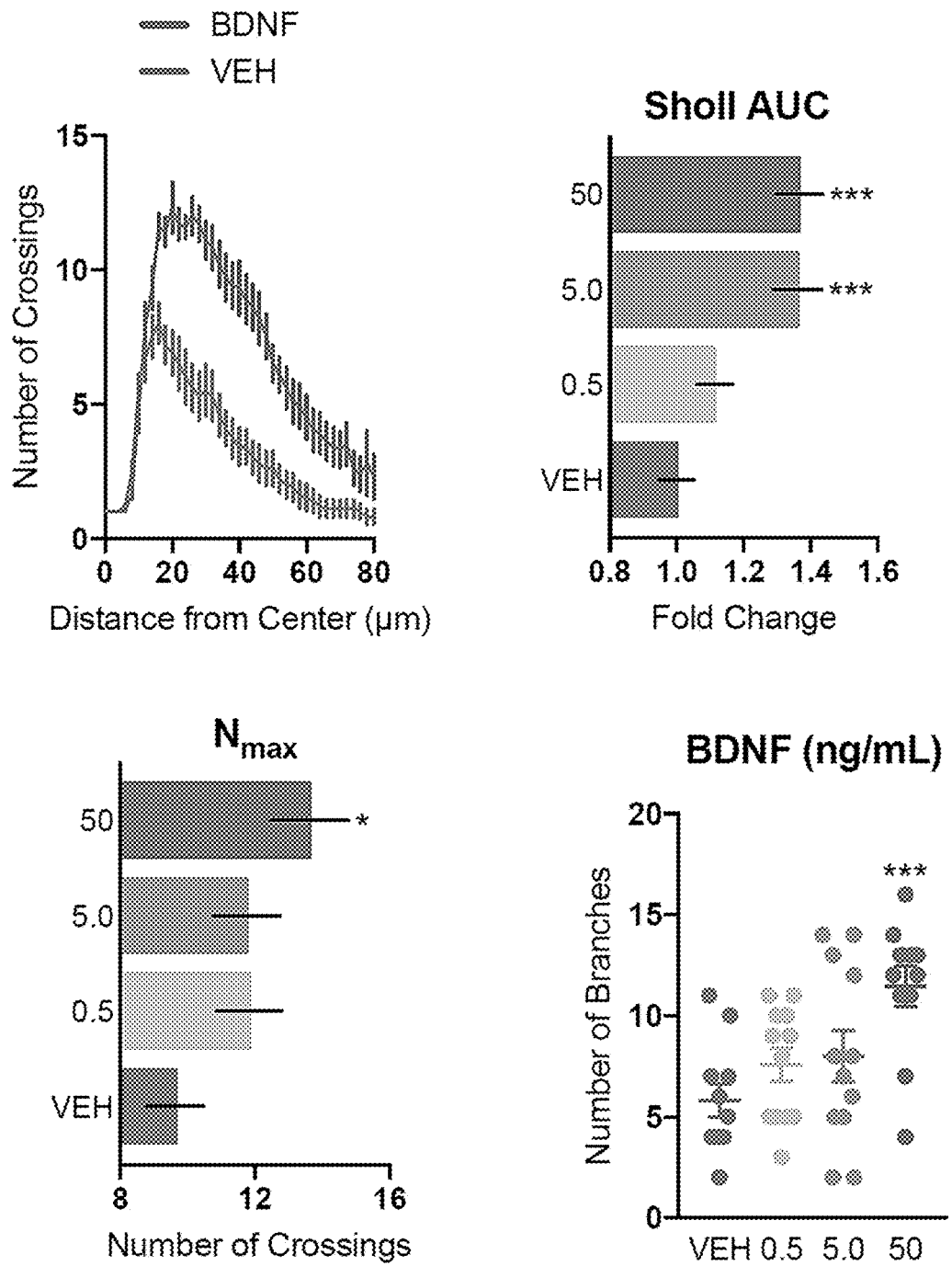
FIG. 4 shows the dose response of recombinant BDNF on neuritogenesis including area under the curve (AUC), maximum number of crossings ($N_{max}$), and number of branches determined from the Sholl plots, respectively (n=11-12 neurons per treatment, 6 days in vitro).

Example 4: Dose-Response Studies of Neuritogenesis Promoted by Lisuride or BDNF A dose-response studies were performed to assess the effects of lisuride on neurite outgrowth in cortical cultures. Surprisingly, a dose response was not clearly observed with lisuride exhibiting activity across 8-orders of magnitude into the femtomolar range (see FIGS. 3A and 3B). This contrasted sharply with the effects of recombinant BDNF on dendritic arbor complexity, as 50 ng/mL of the neurotrophin was significantly less potent following a 100-fold dilution (see FIG. 4).

Example 5: In Vivo Studies of Neuritogenesis

The non-hallucinogenic analogs of tryptamine and ergoline psychedelics are tested in vivo for the effects of the compounds on neuritogenesis. *Drosophila* larvae during various instars are treated with the compound according to the *Drosophila* experiments as described in Example 2.5. Alternatively, zebrafish embryos are treated with the compound according to the zebrafish experiments as described in Example 2.6.

Example 6: In Vivo Studies of Spinogenesis

The non-hallucinogenic analogs of tryptamine and ergoline psychedelics are tested in vivo for the effects of the compounds on spinogenesis in the mPFC of adult rats using Golgi-Cox staining, as described in Example 2.11.

Example 7: In Vivo Studies of Synaptogenesis

The non-hallucinogenic analogs of tryptamine and ergoline psychedelics are tested in vivo for the effects of the compounds on synaptogenesis using electrophysiology method, as described in Example 2.12.

Example 8: Modulation of Neurotrophic Factors (e.g., BDNF)

Figure 5:
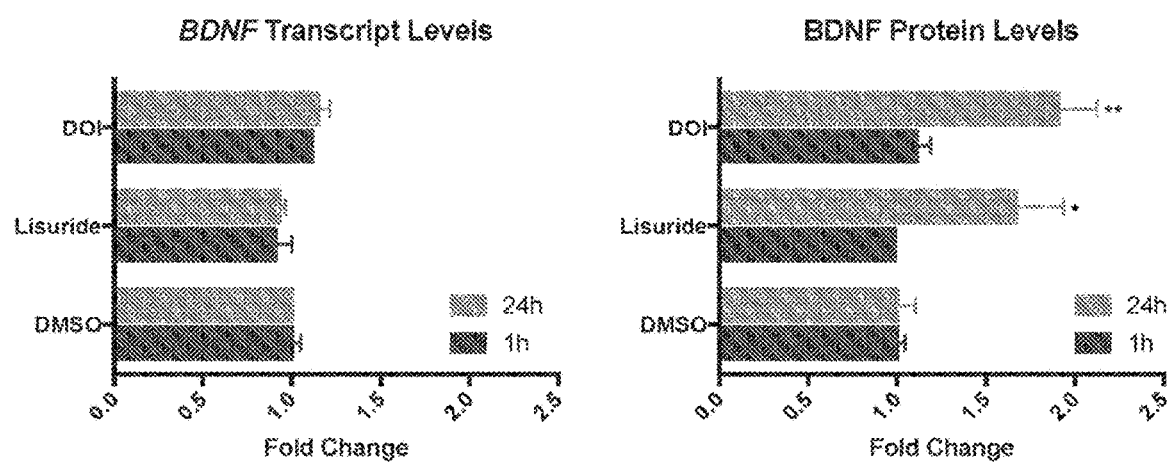
FIG. 5 shows the effects of compounds on BDNF transcript and protein levels after 1 hour or 24 hour treatment.

Cortical neurons were treated with lisuride for 1 hour or 24 hours before measuring gene and protein expression of BDNF using droplet digital PCR (ddPCR) (Example 2.10) and ELISA (Example 2.9), respectively. The expression of BDNF transcript or the protein level of BDNF was measured at 1 hour or 24 hours. After 24 hours, the treatment with lisuride increased the protein levels of BDNF protein, but not the transcript levels of BDNF protein, as shown in FIG. 5.

In addition, Cortical neurons are treated with BDNF, the compound, and a combination of the two, to assess if they have any additive or synergistic effects.

Example 9: Role of TrkB Signaling

Figure 6:
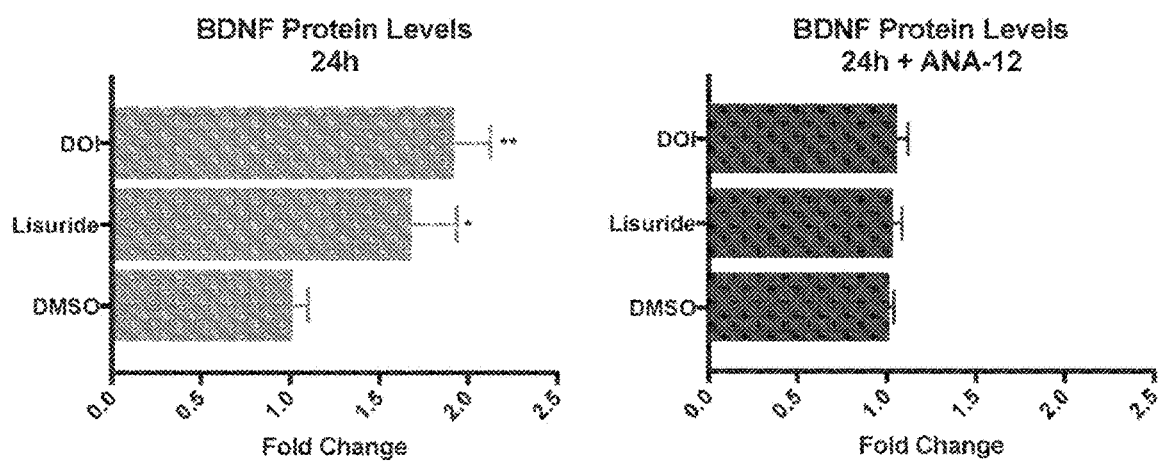
FIG. 6 shows the effects of compounds on BDNF levels in the presence of a TrKB receptor antagonist (ANA-12) after 24 hour treatment.

Psychedelics may facilitate the secretion of BDNF, which in turn binds to cell surface TrkB receptors, leading to additional effects such as the increase in BDNF translation and structural plasticity observed at later time points. Cortical cultures with ANA-12, a selective antagonist of TrkB (BDNF's high affinity receptor), were treated with lisuride to assess if it blocks the ability of the compound to stimulate neuritogenesis and spinogenesis. The results demonstrate that blocking TrkB with an antagonist negates the increase in BDNF protein levels that normally follow a 24 h treatment with lisuride, as shown in FIG. 6.

Furthermore, activation of TrkB is known to promote signaling through mTOR, which plays a key role in structural plasticity, the production of proteins necessary for synaptogenesis. Cortical cultures treated with the compound (e.g., lisuride) are further treated with rapamycin, an mTOR inhibitor, to assess if rapamycin completely blocks the compound-induced neuritogenesis. This approach is to confirm if mTOR activation plays a role in the effects of non-hallucinogenic analogs of the psychedelic compound.

Example 10: Pharmacology and Antagonist Studies

As the 5HT2A receptor has been notoriously associated with the hallucinogenic effects, it is studied to assess if the 5HT2A receptor play a role of promoting in the plasticity-promoting effects of the non-hallucinogenic analog of the psychedelic compound. Accordingly, cortical cultures with ketanserin, an antagonist of the 5HT2A receptor, are treated with lisuride.

Figure 7:
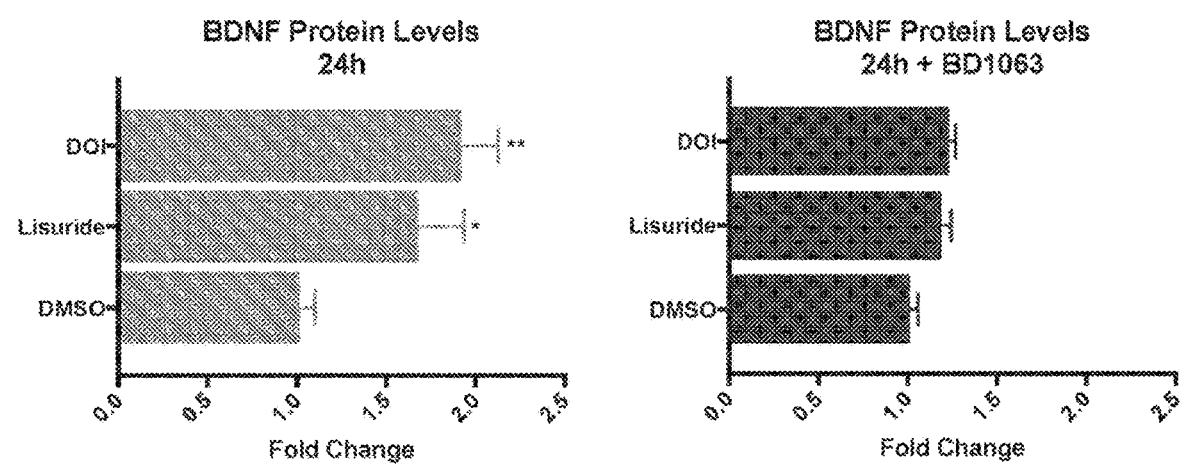
FIG. 7 shows the effects of compounds on BDNF levels in the presence of a Sigma-1 receptor antagonist (BD1063) after 24 hour treatment.

Besides 5HT2A receptors, psychedelics also exhibit high affinity for sigma receptors. While these receptors are quite enigmatic, they are highly expressed in the brain and have been indirectly linked to BDNF signaling. Therefore, cultured cortical neurons were co-treated with the sigma antagonist BD1063 and lisuride. It was found that BD1063 completely blocked the increased translation of BDNF induced by lisuride, as shown in FIG. 7.

Example 11: Membrane-Permeability Studies

Dimethylergoline or trimethyltryptamine analogs can be synthesized and serve as membrane-impermeable analogs of the non-hallucinogenic ergoline or tryptamine psychedelics, respectively.

Control experiments are performed to ensure that these charged species cannot cross membranes but can still bind to their cognate receptors. Such assays include radioligand binding and parallel artificial membrane permeability assays (PAMPAs).

Neuritogenesis studies, as described in Example 2.4, are performed for dimethylergoline or trimethyltryptamine analogs as well as the non-hallucinogenic ergoline or tryptamine psychedelics for comparison.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating depression in a subject in need thereof, comprising administering to the subject in need thereof a therapeutically effective amount of a non-hallucinogenic analog of dimethyltryptamine (DMT) having the structure of Formula (IIa-1):

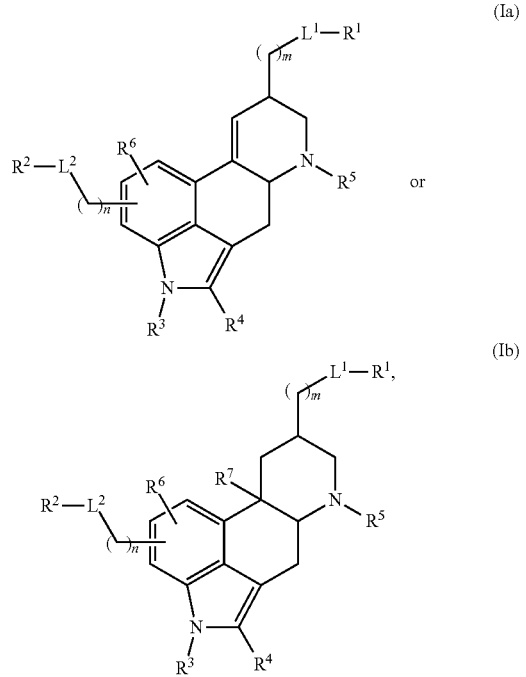

thereby treating depression in the subject in need thereof, wherein:

$L^3$ is a bond, —C(O)NR$^b$—, —NR$^b$C(O)—, —NHC(O)NR$^b$—, —C(O)O—, —OC(O)—, —NHC(O)O—, —SO$_2$NR$^b$—, —NHSO$_2$—, —SO$_2$—, —S—, or —NR$^b$—;

$R^8$ is hydrogen, halogen, $C_1$-$C_6$ alkyl, $C_2$-$C_6$ alkenyl, $C_3$-$C_8$ cycloalkyl, $C_1$-$C_6$ haloalkyl, $C_1$-$C_6$ hydroxyalkyl, $C_1$-$C_6$ alkoxy, $C_1$-$C_6$ aminoalkyl, heterocycloalkyl, aryl, or heteroaryl;

$R^b$ is hydrogen, or $C_1$-$C_6$ alkyl;

$R^{11}$ is di-($C_1$-$C_6$ alkyl)amino;

$R^{12}$ is hydrogen, halogen, —OH, $C_1$-$C_6$ alkyl, $C_1$-$C_6$ haloalkyl, $C_1$-$C_6$ hydroxyalkyl, or $C_1$-$C_6$ alkoxy;

subscript p is 2; and subscript q is an integer from 0 to 3, and wherein the non-hallucinogenic analog of DMT produces a maximum number of dendritic crossings with an increase of greater than 1.0 fold by a Sholl Analysis, wherein the non-hallucinogenic analog of DMT produces an area-under-curve (AUC) of a Sholl plot with an increase of greater than 1.0 fold, wherein the non-hallucinogenic analog of DMT produces a number of dendritic branches with an increase of greater than 1.0 fold, wherein the non-hallucinogenic analog of DMT produces a total dendritic length with an increase of greater than 1.0 fold, wherein the non-hallucinogenic analog of DMT produces a density of dendritic spines with an increase of greater than 1.0 fold, or wherein the non-hallucinogenic analog of DMT produces a density of synapses with an increase of greater than 1.0 fold.

2. The method of claim 1, wherein the non-hallucinogenic analog of DMT is rizatriptan, 6-methoxy-DMT, or 6-fluoro-DMT.

3. The method of claim 1, wherein the non-hallucinogenic analog of DMT produces a density of a presynaptic protein with an increase of greater than 1.0 fold, wherein the presynaptic protein is Vesicular glutamate transporter 1 (VGLUT1).

4. The method of claim 1, wherein the non-hallucinogenic analog of DMT produces a translation of the brain-derived neurotrophic factor (BDNF) with an increase of greater than 1.0 fold.

* * * * *

UNITED STATES PATENT AND TRADEMARK OFFICE
CERTIFICATE OF CORRECTION

PATENT NO. : 12,343,337 B2
APPLICATION NO. : 16/337698
DATED : July 1, 2025
INVENTOR(S) : David E. Olson Page 1 of 1

It is certified that error appears in the above-identified patent and that said Letters Patent is hereby corrected as shown below:

In the Claims

Claim 1, Column 47, Lines 25-53, please delete "

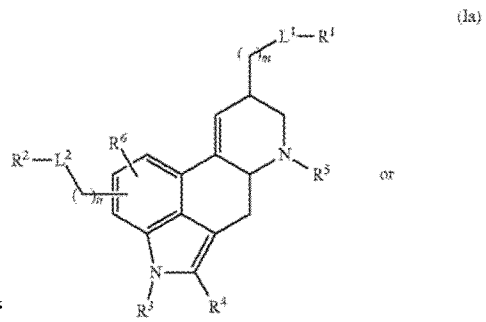

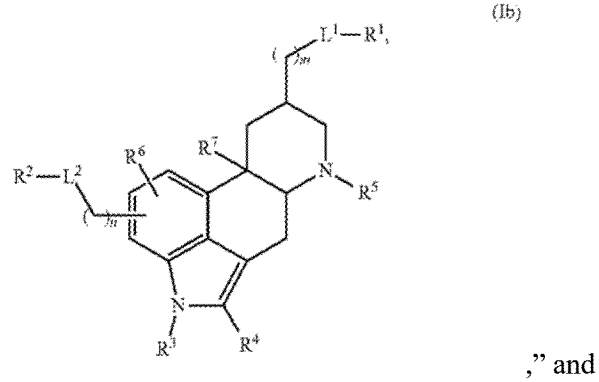

," and insert --

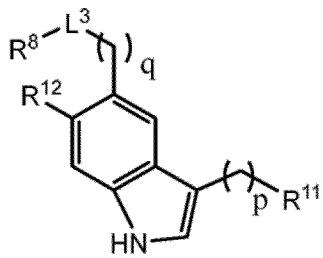

--.

Signed and Sealed this
Tenth Day of February, 2026

John A. Squires
*Director of the United States Patent and Trademark Office*